US012588946B2

(12) United States Patent (10) Patent No.: US 12,588,946 B2
Romoscanu et al. (45) Date of Patent: Mar. 31, 2026

(54) CATHETER DISTAL FORCE SENSOR

(71) Applicants:INCITE MEDICAL SARL, Geneva (CH); Norbert Sylvain Giraud, Bellecombe-en-Bauges (FR); Nicolas Paul Gabriel Guinamard, Menthonnex sous Clermont (FR)

(72) Inventors: Alexandre Ioan Romoscanu, Geneva (CH); Norbert Sylvain Giraud, Bellecombe-en-Bauges (FR); Nicolas Paul Gabriel Guinamard, Menthonnex sous Clermont (FR)

(73) Assignees: INCITE MEDICAL SARL, Geneva (CH); Norbert Sylvain Giraud, Bellecombe-en Bauges (FR); Nicolas Paul Gabriel Guinamard, Menthonnex sous Clermont (FR)

( * ) Notice: Subject to any disclaimer, the term of this patent is extended or adjusted under 35 U.S.C. 154(b) by 674 days.

(21) Appl. No.: 17/917,471

(22) PCT Filed: Apr. 8, 2021

(86) PCT No.: PCT/IB2021/052912
§ 371 (c)(1),
(2) Date: Oct. 6, 2022

(87) PCT Pub. No.: WO2021/205373
PCT Pub. Date: Oct. 14, 2021

(65) Prior Publication Data
US 2023/0165655 A1 Jun. 1, 2023

Related U.S. Application Data

(60) Provisional application No. 63/017,726, filed on Apr. 30, 2020, provisional application No. 63/006,742, filed on Apr. 8, 2020.

(51) Int. Cl.
*A61B 18/14* (2006.01)
*A61B 34/00* (2016.01)
(Continued)

(52) U.S. Cl.
CPC .......... *A61B 18/1492* (2013.01); *A61B 34/76* (2016.02); *A61B 90/06* (2016.02);
(Continued)

(58) Field of Classification Search
CPC . G01L 5/166; G01L 1/24; G01L 1/247; G01L 1/25; A61B 5/8652; A61B 5/0084;
(Continued)

(56) References Cited

U.S. PATENT DOCUMENTS 10,888,391 B2 1/2021 Ruppersberg
2005/0082466 A1* 4/2005 Smith ................... G01B 11/16
250/227.11

(Continued)

*Primary Examiner* — Benjamin R Schmitt
(74) *Attorney, Agent, or Firm* — Christensen, Fonder, Dardi & Herbert PLLC; John P. Fonder

(57) ABSTRACT

A force sensor assembly for use in the field of cardiac ablation, for the ablation-based treatment of atrial fibrillation and other cardiac arrhythmias. Various embodiments of the disclosure are directed to a catheter distal force sensor for measuring catheter tip-to-endocardial wall force by measuring displacement of irradiation patterns sensed with a two-dimensional imaging sensor. The disclosed devices sense an array of irradiation pattern characteristics, including changes in size and location of irradiation shapes of the irradiation pattern. In some embodiments, multiple irradiation spots are tracked with the two-dimensional imaging sensor to infer the components of a reaction force vector acting the force sensor assembly. The disclosed force is designed to accommodate typical catheter tip dimensions, the outer diameter of these usually being less than or equal to 3 mm.

20 Claims, 10 Drawing Sheets

(51) Int. Cl.

| | |
|---|---|
| *A61B 90/00* | (2016.01) |
| *G01L 5/166* | (2020.01) |
| *A61B 18/00* | (2006.01) |
| *G01L 1/24* | (2006.01) |
| *G01L 1/25* | (2006.01) |

(52) U.S. Cl.
CPC .... *G01L 5/166* (2013.01); *A61B 2018/00577* (2013.01); *A61B 2018/1407* (2013.01); *A61B 2018/1467* (2013.01); *A61B 2090/065* (2016.02); *G01L 1/24* (2013.01); *G01L 1/25* (2013.01)

(58) Field of Classification Search
CPC ..... A61B 90/06; A61B 18/1492; A61B 34/76; A61B 2090/065
USPC .................................................. 73/862.624
See application file for complete search history.

(56) References Cited

U.S. PATENT DOCUMENTS

| | | | |
|---|---|---|---|
| 2008/0294144 A1 | 11/2008 | Leo et al. | |
| 2010/0094163 A1 | 4/2010 | Deladi et al. | |
| 2012/0265102 A1 | 10/2012 | Leo et al. | |
| 2014/0209797 A1 * | 7/2014 | Klimovitch | A61B 90/06 |
| | | | 250/227.14 |
| 2015/0272443 A1 | 10/2015 | Sliwa et al. | |
| 2016/0367330 A1 | 12/2016 | Klimovitch | |
| 2019/0011317 A1 | 1/2019 | Toussaint et al. | |
| 2019/0161119 A1 | 5/2019 | Greenwood et al. | |

* cited by examiner

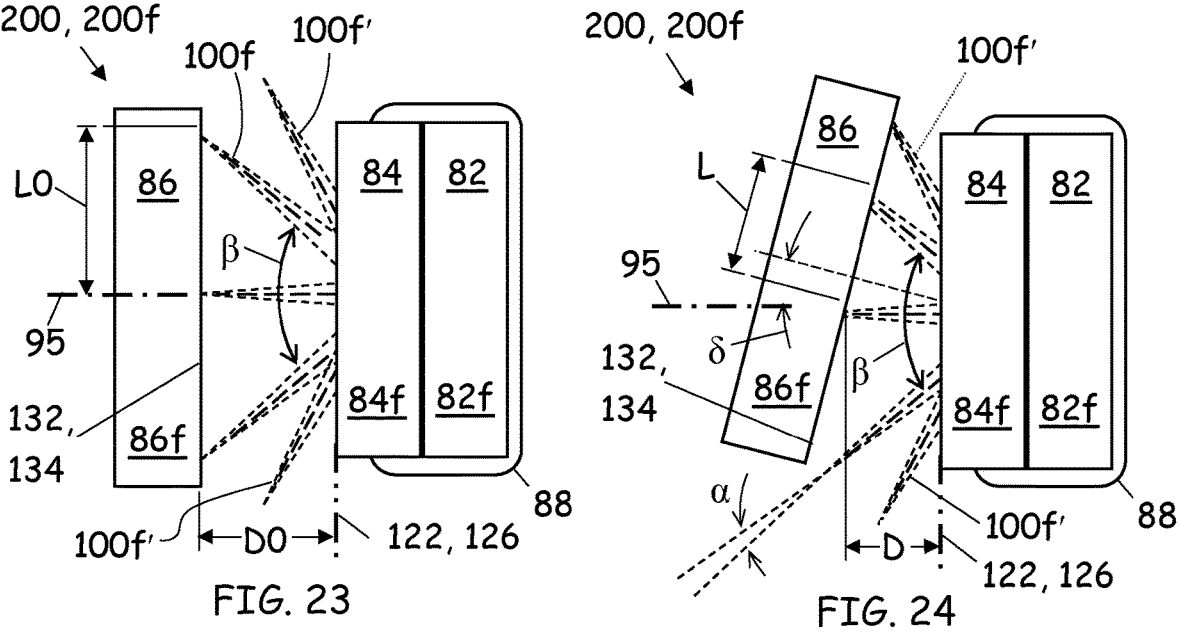
FIG. 23
FIG. 24
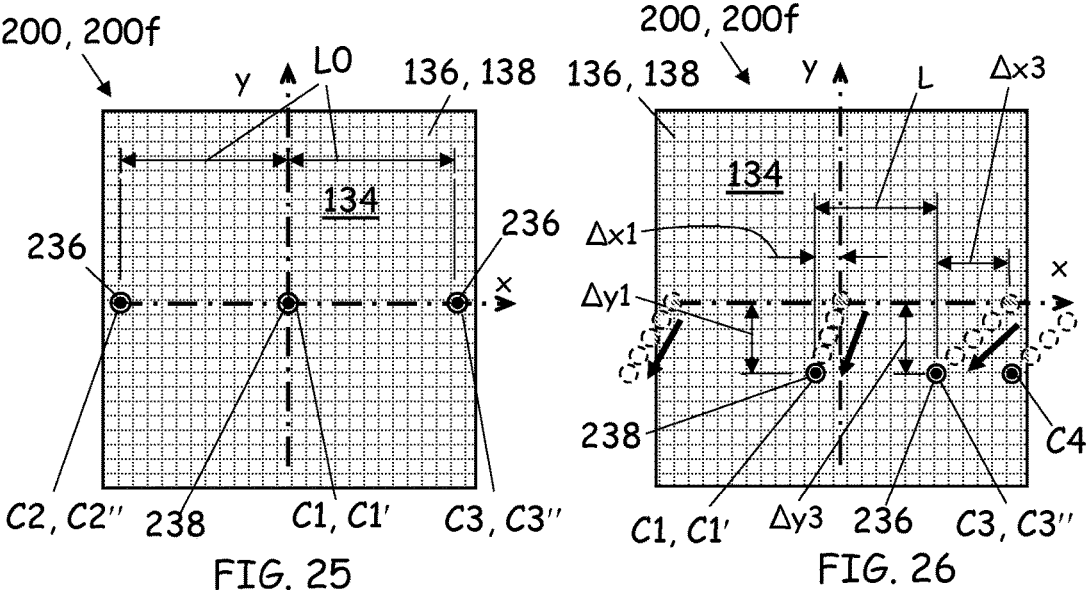
FIG. 25
FIG. 26

CATHETER DISTAL FORCE SENSOR

RELATED APPLICATIONS

This application is a National Stage filing of PCT Application No. PCT/IB2021/052912 filed Apr. 8, 2021, which claims the benefit of U.S. Provisional Application No. 63/006,742, filed Apr. 8, 2020, and of U.S. Provisional Application No. 63/017,726, filed Apr. 30, 2020, the disclosures of which are incorporated by reference herein in their entirety.

FIELD OF THE DISCLOSURE

This disclosure is directed generally to a force sensor for catheters and more specifically to such assemblies utilizing displacement of optical beams.

BACKGROUND

Catheter ablation of atrial fibrillation or other cardiac arrhythmias implementing thermal energy techniques such as radiofrequency (RF), as well as electroporation techniques, benefit from a tip-to-endocardial wall applied force feedback to the user, who may manually operate the catheter by means of a proximally located control handle. Real time feedback of the tip-to-endocardial wall applied force is beneficial for several reasons. For example, in the absence of a good contact, ablation effectiveness is impaired, and an improved contact should be attempted before ablation is performed. A minimum force, indicating adequate contact between catheter tip and the endocardial wall enhances the effectiveness of ablation. On the other hand, excessive force raises the risk of heart wall perforation (tamponade). In PVI (pulmonary vein isolation) procedures, a force in excess of 50 gf (gram-force) is generally considered as creating a risk of tamponade. Accordingly, in PVI procedures, an application force of about 10 gf or 20 gf is considered a good catheter tip-to-endocardial wall contact. The "gf" (gram-force) is a unit of measure of force which is commonly used in the art, with one gf equal to 0.00981 Newton.

Also, the extent of the lesion (depth, width) has been shown as depending on several parameters, such as the ablation power and the ablation time, but also the force. Knowledge of the force allows established ablation metrics such as LSI (lesion size index) or FTI (force time integral) to be used for an improved control of the ablation extent. See, for example, De Mattia et. al. (2018), "Prospective Evaluation of Lesion Index-Guided Pulmonary Vein Isolation Technique in Patients with Paroxysmal Atrial Fibrillation: 1-year Follow-Up.", J Atr Fibrillation 10(6): 1858, and Kautzner et al. (2015), "EFFICAS II: optimization of catheter contact force improves outcome of pulmonary vein isolation for paroxysmal atrial fibrillation", Europace 17(8): 1229-1235, the disclosures of which are incorporated by reference herein, except for express definitions contained therein. In addition, knowledge of the catheter tip-to-endocardial wall applied force is also useful in the context of cardiac topographic mapping.

SUMMARY OF THE DISCLOSURE

A force sensor assembly is disclosed for use with percutaneous devices, for example point-by-point (focal) ablation-based treatment of atrial fibrillation and other cardiac arrhythmias. Such point-by-point ablation catheters, linear in shape, can be unidirectional, bidirectional, multidirectional, or non-steerable (i.e. steered by a steerable sheath or other techniques). Various embodiments of the disclosure are directed to a catheter distal force sensor for measuring catheter tip-to-endocardial wall force by measuring displacement of irradiation patterns sensed with a two-dimensional imaging sensor. The disclosed devices sense an array of irradiation pattern characteristics, including changes in size and location of irradiation shapes of the irradiation pattern. In some embodiments, multiple irradiation spots are tracked with the two-dimensional imaging sensor to infer the orthogonal components of a reaction force vector acting on the force sensor assembly. The disclosed force is designed to accommodate typical catheter tip dimensions, the outer diameter of these usually being less than or equal to 9 French (3 mm). The measured force typically ranges from 0 to 200 gf in modulus.

The force sensing assembly detects reaction forces exerted thereon by measuring the displacement of irradiation patterns that are radiatively coupled to a two-dimensional imaging sensor. The concept has been previously disclosed in U.S. Pat. No. 10,888,391 to Ruppersberg, the disclosure of which is hereby incorporated by reference herein in its entirety except for patent claims and express definitions contained therein. Ruppersberg discloses detection of a single diverging beam of light radiatively coupled to an optical sensor that changes in size and central location response to applied forces.

In some embodiments of the present disclosure, a plurality of beams of electromagnetic radiation are radiatively coupled with a 2D (two-dimensional) image sensor, the beams forming an irradiation pattern formed on the 2D image sensor that changes in response to reaction force vectors imposed on force sensor assembly. By using a plurality of beams, the resolution of the force vector can be accomplished by measuring the displacement paired coordinates x,y that indicate the positions of the respective beams within the irradiation pattern. In some embodiments, the irradiation pattern may include a plurality of irradiation spots of sufficiently small size to enable detection of their position without resorting to extensive weighted averaging techniques used for locating centroids of larger irradiation shapes. The small irradiation spot sizes, which may be smaller than state of the art irradiation shapes by an order of magnitude or more, avoids the complications associated with area-weighted centroids, such as detector border effects, irradiation shape geometry, and radiation intensity measurements. Also, the smaller spot sizes provides increased radiation flux at the irradiated pixels of the sensor, as the energy isn't spread over the comparatively larger areas of conventional irradiation shapes. The use of multiple small irradiation spots also enables a wider range of displacement on the detection plane of the 2D force sensor, as the irradiation spots can move closer to the edges of the detection plane without losing valuable information otherwise needed for computation of irradiation shape sizes and centroids.

Alternative embodiments utilize more moderate sized irradiation shapes, or a mixture of small irradiation spots and moderate sized irradiation shapes, providing redundant information for averaging techniques, for example, to improve sensitivity and/or signal-to-noise ratios.

Structurally, various embodiments of the disclosure are directed to a force sensor assembly for a percutaneous device, comprising a deformable body including a proximal portion and a distal portion, the proximal portion defining and being concentric about a central axis, an image sensing module physically coupled to one of the proximal portion and the distal portion, the image sensing module including a two-dimensional image sensor that defines a detection plane, an emitter assembly physically coupled to an other of the distal portion and the proximal portion, and an optical arrangement coupled to the emitter assembly and configured to receive electromagnetic radiation from the emitter assembly, wherein the optical arrangement is configured to form the electromagnetic radiation into a plurality of beams that are subtended by the detection plane of the two-dimensional image sensor to define an irradiation pattern on the two-dimensional image sensor, the deformable body is configured for a deformation in response to a force applied to the distal portion, the deformation including translation of the distal portion along the central axis in response to an axial component of the force and a rotational deflection of the distal portion away from the central axis in response to a lateral force, and the irradiation pattern dynamically changes on the detection plane in response to the deformation, the dynamic change in the irradiation pattern being detected by the two-dimensional image sensor.

In some embodiments, one of the plurality of beams subtended by the detection plane defines an irradiation shape that having a first dimension, a second dimension orthogonal to the first dimension, and an irradiation shape centroid, the dynamic change in the irradiation pattern including a positional displacement of the irradiation shape centroid and a change in at least one of the first dimension and the second dimension of the irradiation shape.

The plurality of beams may include a canted beam that defines a propagation axis that is incident on the detection plane to define an incidence angle relative to a normal vector of the detection plane when the force sensor assembly is in an unloaded state, wherein the incidence angle is an acute angle. A corresponding emitter of the canted beam is affixed to an optical mount of the force sensor assembly to align with the incidence angle. In some embodiments, a corresponding emitter of the canted beam is affixed to an optical mount of the force sensor assembly to align parallel to the normal vector of the detection plane, the optical arrangement being configured to redirect the canted beam to define the incidence angle.

In some embodiments, the plurality of beams includes a divergent beam. The divergent beam defines a profile angle that is in a range from 30 degrees to 150 degrees inclusive, or defines a profile angle that is an acute angle.

In some embodiments, the irradiation pattern includes an irradiation spot that defines an irradiation spot centroid, the dynamic change of the irradiation pattern including a positional displacement of the irradiation spot centroid. The positional displacement of the irradiation spot may be in response to the rotational deflection of the distal portion of the deformable body. In some embodiments, a corresponding beam of the plurality of beams that conveys the irradiation spot defines a profile angle that is in a range from one to 4 degrees inclusive. The irradiation spot may define a maximum dimension that is in a range of three micrometers to 15 micrometers inclusive. In some embodiments, the irradiation spot centroid is approximated as a position of a pixel of the two-dimensional image sensor that is irradiated by the irradiation spot and generates a local maximum signal.

In some embodiments, the irradiation pattern includes a plurality of irradiation spots, each defining a respective irradiation spot centroid, the dynamic change of the irradiation pattern including a positional displacement of a designated one of the irradiation spot centroids and a difference between positional displacements of at least two of the irradiation spot centroids. In some embodiments, at least two of the plurality of beams define respective propagation axes that define an open angle that faces the detection plane. The at least two of the plurality of beams may intersect between the optical arrangement and the two-dimensional image sensor. In some embodiments, the positional displacement of the designated one of the irradiation spot centroids is in response to the rotational deflection of the distal portion. The difference between positional displacements of the at least two of the irradiation spot centroids may be in response to the translation of the distal portion of the deformable body along the central axis.

In some embodiments, each of the plurality of beams corresponding to the plurality of irradiation spots defines a respective profile angle that is in a range from one to four degrees inclusive. In some embodiments, each of the plurality of irradiation spots defines a respective maximum dimension that is in a range of three to 15 micrometers inclusive. Each of the plurality of irradiation spot centroids may be approximated as a position of a pixel of the two-dimensional image sensor that is irradiated by a corresponding one of the plurality of irradiation spots and generates a respective local maximum signal.

In some embodiments, the deformable body includes a compliant mid-portion that separates the proximal end from the distal end, the compliant mid-portion being more compliant than the proximal portion or the distal portion to accommodate the deformation of the deformable body. Alternatively, the distal portion may be more compliant than the proximal portion to accommodate the deformation of the deformable body.

In some embodiments, electromagnetic radiation from the emitter assembly is sourced local by local emitters. The local emitters may be powered by a remote electrical energy source. The local emitters may be one of a vertical-cavity surface-emitting laser, an edge-emitting laser, and a light-emitting diode.

In some embodiments, the electromagnetic radiation from the emitter assembly is sourced by an emission source, which may be located remotely. The electromagnetic radiation may be conveyed to the emitter assembly via an optical fiber link.

The emitter assembly may be a unitary component. or a plurality of distributed components. Likewise, the optical arrangement may be a unitary component. or a plurality of distributed components. The image sensor is one of a complementary metal oxide semiconductor and a charged coupled device. In some embodiments, the electromagnetic radiation is transmitted at one or more wavelengths that are in a range from ultraviolet to infrared inclusive. The force sensor assembly may be housed in a distal end portion of a catheter.

The catheter may be one of unidirectional, bidirectional, and multidirectional, and may include a plurality of ring electrodes. In some embodiments, the distal end portion of the deformable body is coupled to a catheter tip. The distal tip may include a smooth surface. In some embodiments, the catheter tip defines a cylindrical base and a hemispherical end at a distal extremity. The distal tip may be an ablation head.

In some embodiments, a control and signal processing system is coupled to the force sensor assembly for processing signals received from the two-dimensional image detector, and may also be coupled to the energy source.

In some embodiments, at least one of the emitter assembly, the optical arrangement, and the energy source is configured to for selective radiative coupling of at least one individual beam of the plurality of beams with the detection plane. The selective radiative coupling may be controlled at a frequency that is within a range of one Hz and 10 Hz inclusive. In some embodiments, the control and processing system controls selective activation of the energy source for the selective radiative coupling.

Various embodiments of the disclosure are directed to a method for resolving a reaction force vector applied on a percutaneous device, comprising configuring a signal processing system for: receiving a first set of signals from a two-dimensional image sensor of a force sensor assembly that corresponds to a first irradiation pattern that includes a plurality of irradiation shapes incident on the two-dimensional image sensor; receiving a second set of signals from the two-dimensional image sensor that corresponds to a second irradiation pattern that includes the plurality of irradiation shapes incident on the two-dimensional image sensor; determining a change in positions of the plurality of irradiation shapes of the second irradiation pattern relative to the plurality of irradiation shapes of the first irradiation pattern; and inferring a force vector applied to the force sensor assembly based on the change in positions.

The method may comprise configuring the signal processing system for resolving a first set of scalar values that characterize the change in positions. In some embodiments, the first set of scalar values represent the change in positions based on a change of position of a centroid of one of the plurality of irradiation spots of the first and second irradiation patterns, and the force vector may be inferred using one of calibration matrix inversion, function fitting, superposition of the first set of scalar values.

The method may comprise configuring the signal processing system for resolving a second set of scalar values, the first set of scalar values characterizing the first irradiation pattern, the second set of scalar values characterizing the second irradiation pattern. In some embodiments, first set of scalar values are taken with the force sensor assembly in an unloaded state, and the second set of scalar values are taken with the force sensor assembly in a loaded state. In some embodiments, the second set of scalar values represent the change in positions based on a change of the second set of scalar values relative to the first set of scalar values. The force vector may be inferred using one of calibration matrix inversion, function fitting, and superposition of the first set of scalar values added to the second set of scalar values.

The method may include configuring the signal processing system for determining a change in size of second irradiation pattern relative to the first irradiation pattern and may include configuring the signal processing system for resolving a first set of scalar values that characterize the change in positions and the change in size. In some embodiments, the first set of scalar values represent the change in positions based on a change of position of a centroid of an irradiation shape of the first and second irradiation patterns, and the first set of scalar values represent the change in size of the irradiation shape of the first and second irradiation patterns. The force vector may be inferred using one of calibration matrix inversion, function fitting, superposition of the first set of scalar values.

In some embodiments, the method includes configuring the signal processing system for resolving a second set of scalar values, the first set of scalar values characterizing the first irradiation pattern, the second set of scalar values characterizing the second irradiation pattern. The first set of scalar values may be taken with the force sensor assembly in an unloaded state, and the second set of scalar values are taken with the force sensor assembly in a loaded state. In some embodiments, the second set of scalar values represent the change in positions and the change in size based on a change of the second set of scalar values relative to the first set of scalar values. The force vector may be inferred using one of calibration matrix inversion, function fitting, and superposition of the first set of scalar values added to the second set of scalar values. In some embodiments, the force vector is resolved in three dimensions, which may be orthogonal to each other.

Various embodiments of the disclosure are directed to a force sensor assembly for a percutaneous device, comprising: a deformable body including a proximal portion and a distal portion, the proximal portion defining and being concentric about a central axis; an image sensing module physically coupled to one of the proximal portion and the distal portion, the image sensing module including a two-dimensional image sensor that defines a detection plane; an emitter assembly physically coupled to an other of the distal portion and the proximal portion; and an optical arrangement coupled to the emitter assembly and configured to receive electromagnetic radiation from the emitter assembly. In some embodiments: the optical arrangement is configured to form the electromagnetic radiation into a single convergent beam subtended by the detection plane of the two-dimensional image sensor to define an irradiation shape on the two-dimensional image sensor; the deformable body is configured for a deformation in response to a force applied to the distal portion, the deformation including translation of the distal portion along the central axis in response to an axial component of the force and a rotational deflection of the distal portion away from the central axis in response to a lateral force; and the irradiation pattern dynamically changes on the detection plane in response to the deformation, the dynamic change in the irradiation pattern being detected by the two-dimensional image sensor. The optical arrangement may define a datum that is coplanar with a designated plane from which the single convergent beam is referenced, the designated plane being orthogonal to the central axis, the single convergent beam defining a focal point that is between the detection plane and the designated plane. In some embodiments, the single convergent beam defines a profile angle that is in a range from 30 degrees to 150 degrees inclusive.

BRIEF DESCRIPTION OF THE DRAWINGS

FIGS. 23 and 24 are schematic views of the operation of a multiple divergent beam configuration that includes auxiliary beams according to an embodiment of the disclosure;

FIGS. 25 and 26 are plan views the irradiation pattern incident on the detection plane of the force sensor assembly corresponding to FIGS. 23 and 24, respectively, according to an embodiment of the disclosure;

DETAILED DESCRIPTION OF THE DRAWINGS

Figure 1:
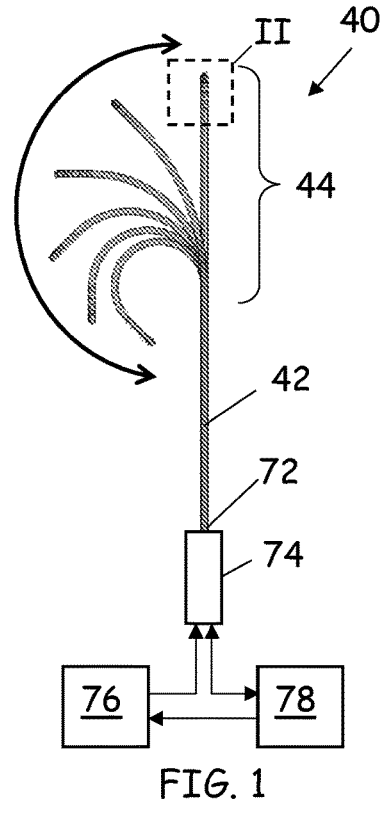
FIG. 1 is a schematic of a force sensing catheter according to an embodiment of the disclosure.
Figure 2:
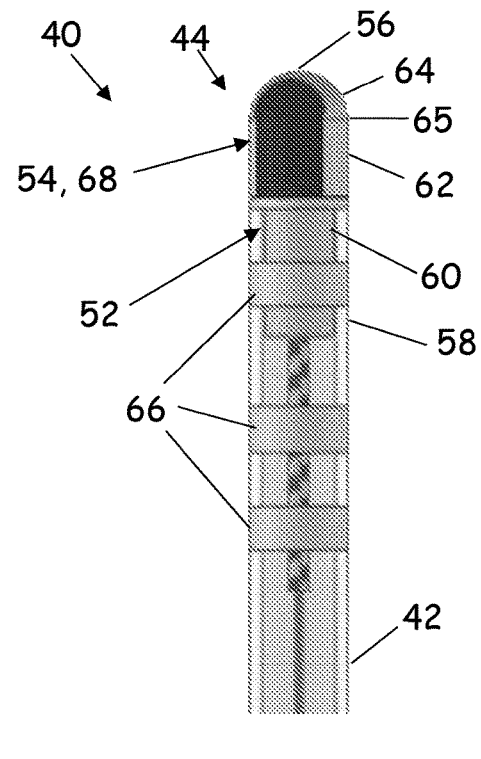
FIG. 2 is an enlarged partial cutaway view of a distal portion of the force sensing catheter of FIG. 1 according to an embodiment of the disclosure.
Figure 3:
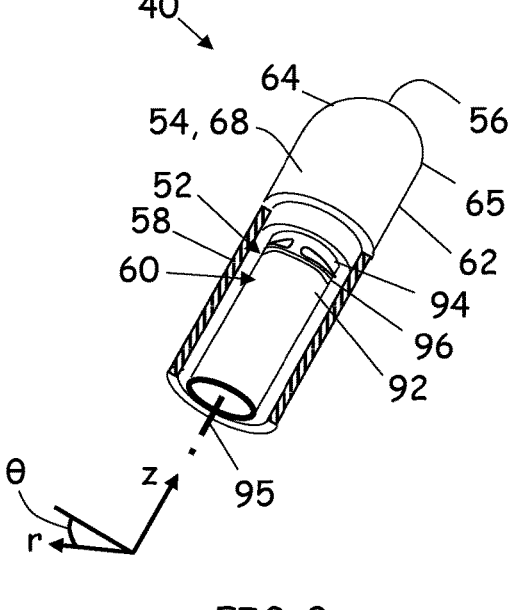
FIG. 3 is an enlarged, perspective cutaway view of the distal portion of FIG. 2 according to an embodiment of the disclosure.

Referring to FIGS. 1 through 3, a force sensing catheter 40 is depicted according to an embodiment of the disclosure. The force sensing catheter 40 includes a catheter shaft 42 having a distal end portion 44. The distal end portion 44 includes a force sensor assembly 52 that is proximal to a distal tip 54, the distal tip 54 being located at a distal extremity 56 of the force sensing catheter 40. In some embodiments, the distal end portion 44 includes an outer shaft 58 that abuts and captures the distal tip 54, and surrounds a deformable body 60 which houses the force sensor assembly 52.

In some embodiments, a proximal end 72 of the catheter shaft 42 is physically coupled to a control handle 74. An energy source 76 may be external to the control handle 74 and routed to the catheter shaft 42 via the control handle 74. Alternatively, the energy source 76 may be housed in a control handle (not depicted). In some embodiments, the energy source 76 is a remote emission source that conveys electromagnetic radiation to the force sensor assembly 52, for example via optical fiber links. The energy source 76 may also include an electrical source that transmits electricity to the force sensor assembly 52 via electrical wiring, the force sensor assembly 52 generating the electromagnetic irradiation locally. The electromagnetic radiation generated either remotely or locally is at a wavelength or wavelengths that is in a range from the ultraviolet through the infrared spectra.

In some embodiments, the control handle 74 interfaces a control and signal processing system 78 that is in communication with the force sensor assembly 52. The control and signal processing system 78 may also interface and control the energy source 76. In some embodiments, the control handle 74 houses a unidirectional steering mechanism (not depicted) to effect the motion depicted in FIG. 1.

In some embodiments, the distal end portion 44 has a length that is in a range of 10 mm (millimeters) to 150 mm inclusive. The distal tip 54 may define an axial length that is in a range of one mm to 10 mm inclusive, and an outer diameter that is less than or equal to 9 French (3 mm). The deformable body 60 may define an axial length that is in a range of one mm to 12 mm inclusive, and an outer diameter that is in a range of one mm to 3 mm inclusive. Herein, a range that is said to be "inclusive" includes the endpoint values of the stated range. Herein, "axial" refers to a direction parallel to a central axis 95 of the force sensor assembly (i.e., parallel to the z-axis of the r-O-z reference coordinate system of FIG. 3). "Lateral" refers to a direction that is orthogonal to the axial direction (i.e., parallel to the r-axis of the r-O-z reference coordinate system of FIG. 3).

The outer shaft 58 may be polymeric, composite, or metallic. In some embodiments, the outer shaft 58 is of a cylindrical or bellows shape. The outer shaft 58 may include an electroformed or hydroformed metallic bellow or similar component (none depicted) that surrounds the deformable body 60 for enhanced axial and lateral compliance. In some embodiments, the outer shaft 58 is integral with the catheter shaft 42.

In some embodiments, the distal tip 54 is made of an electrically conducting material, such as platinum-iridium, stainless steel, titanium, gold or combinations thereof. In some embodiments, the distal tip 54 is fabricated to form a substrate material of one metal or alloy that is plated with another metal or alloy. The distal tip 54 may include a cylindrical base 62 with the distal extremity 56 defining a hemispherical end 64. The distal tip 54, or at least the distal extremity 56, may have a smooth surface 65. In some embodiments, the smooth surface 65 is finished to an ISO grade N8 surface finish or smoother. In some embodiments, the smooth surface 65 is finished to an ISO grade N5 surface finish or smoother.

The distal end portion 44 may include a plurality of ring electrodes 66 proximal to the distal tip 54. In some embodiments, the distal tip 54 is configured as an ablation head 68, and may include distally open irrigation channels or a closed-circuit cooling arrangement (neither being depicted). The distal tip 54 may also include one or more temperature sensing elements (not depicted), such as a thermocouple(s) or thermistor(s).

Functionally, the outer shaft 58 protects and isolates the force sensor assembly 52 and other internal components of the force sensing catheter 40 from the surrounding environment, while still enabling enhanced mechanical compliance of the force sensor assembly 52 both axially and laterally. In some embodiments, the deformable body 60 is physically isolated from the outer shaft 58 for better functionality of the force sensor assembly 52 (e.g., less hysteresis). The distal tip 54, when configured as the ablation head 68, may be used for ablation. The irrigation capability, when present, can limit the build-up of charring at the ablation head 68. The ring electrodes 76 may be used for mapping and diagnostics. The force sensor assembly 52 disclosed herein may also be configured for use in other percutaneous devices (e.g., renal denervation RF ablation). The steering mechanism (not depicted) of the force sensing catheter 40 enables articulation of the distal end 44 of the catheter shaft 42 to take on arcuate configurations, such as illustrated in FIG. 1.

Figure 4:
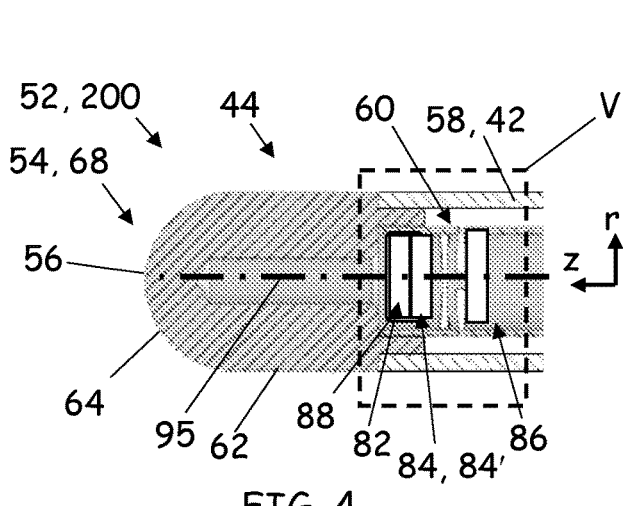
FIG. 4 is a partial sectional view of a distal portion of a force sensing catheter utilizing one of a beam configuration and a multiple beam configuration according to an embodiment of the disclosure.
Figures 5, 6:
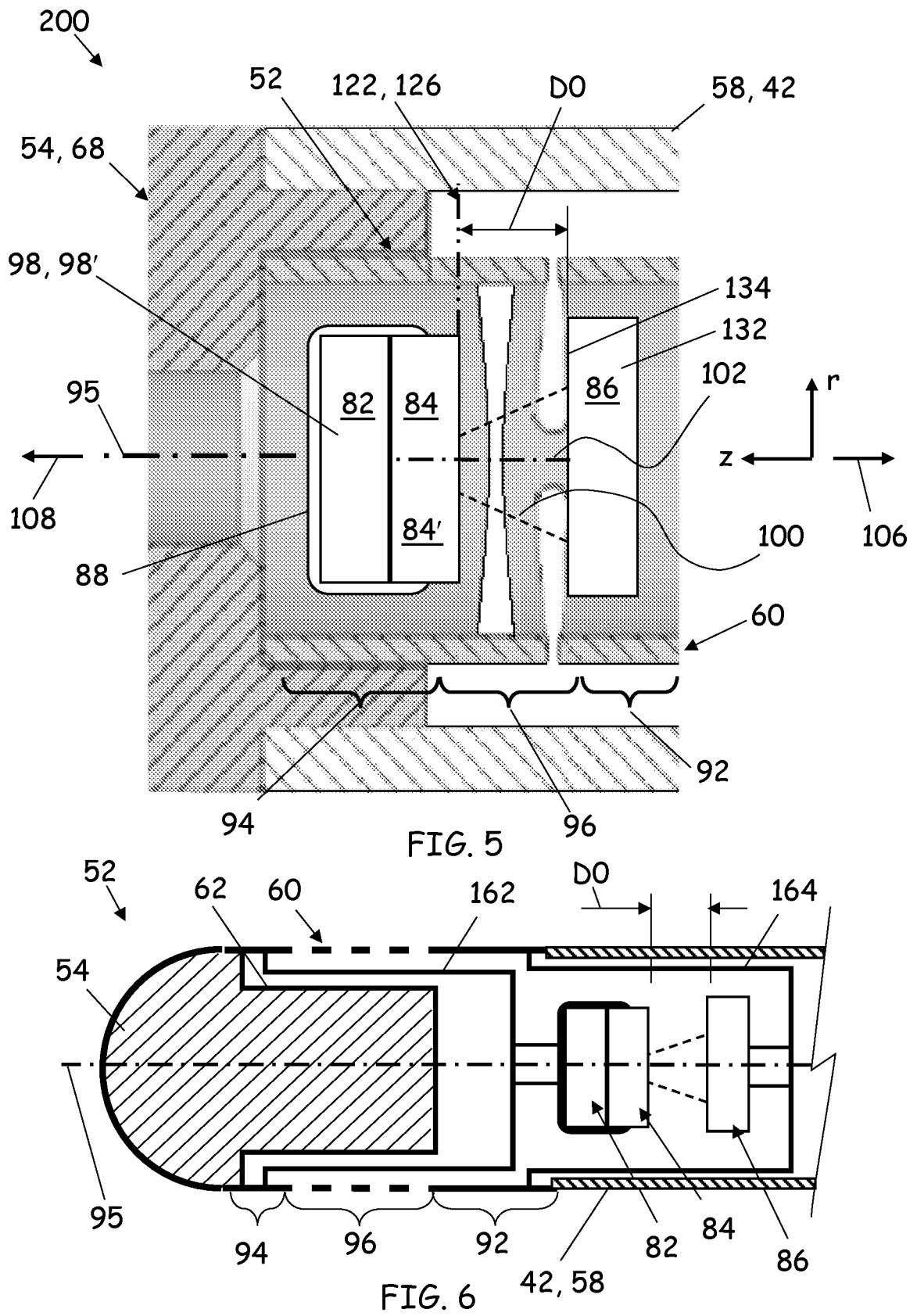
FIG. 5 is an enlarged view of FIG. 4 at inset V according to an embodiment of the disclosure.
FIG. 6 is a sectional schematic of a force sensor assembly with offset structures for locating optical components proximal to the deformable body according to an embodiment of the disclosure.

Referring to FIGS. 4 and 5, the force sensor assembly 52 is depicted according to an embodiment of the disclosure. The force sensor assembly 52 includes the deformable body 60, an emitter assembly 82 radiatively coupled to an optical arrangement 84, and an image sensing module 86 radiatively coupled to the optical arrangement 84. Physical coupling and arrangements of the emitter assembly 82 and optical arrangement 84 may be secured by an optical mount 88.

The deformable body 60 may include a proximal portion 92 and a distal portion 94, with the proximal portion 92 defining and being concentric with a central axis 95 of the force sensor assembly 52. In some embodiments, the deformable body 60 may be located at the distal end of, and thus be part of, a longer component which expands into the catheter portion 44, and which can be used for catheter steering.

The central axis 95 may be coincident with a z-axis of an r-O-z reference coordinate system (FIG. 3). The r-O-z reference coordinate system may be of arbitrary origin along the central axis 95. The r-O-z reference coordinate system is fixed relative to the proximal portion 92, and therefore floats along with the proximal portion 92. As such, in the context of the present disclosure, the proximal portion 92 of the deformable body 60 may be assumed as fixed, while the distal portion 94 (and distal tip 54) can move relative thereto within a limited range. Because of the mechanical compliance of the deformable body 60 in the axial and lateral directions, the relative position and orientation between the image sensing module 86 and emitter assembly 82 and the optical arrangement 84 changes with changing force applied on the distal tip 54.

In some embodiments, the proximal and distal portions 92 and 94 are separated by a compliant mid-portion 96. The distal portion 94 may be physically coupled to the distal tip 54 in a rigid or compliant manner. The proximal portion 92 may be physically coupled to the catheter shaft 42. The compliant mid-portion 96, when utilized, is characterized by an enhanced compliance to both axial and lateral deformations relative to the proximal and distal portions 92, 94.

For the force sensor assembly 52, the emitter assembly 82 is directly or locally sourced. That is, the emitter assembly 82 for the force sensor assembly 52 includes an emitter or emitters 98 that generates electromagnetic radiation locally, which passes through the optical arrangement 84 to form a beam or beams 100 of electromagnetic radiation. Each beam 100 is centered about a respective propagation axis 102 and may be incident on the image sensing module 86. The emitters 98 may receive electrical power via electrical conductors that extend proximally from the emitter assembly 82 through the force sensing catheter 40 and are connected to the energy source 76, the energy source 76 being an electrical source. Non-limiting examples of local emitters 98 of the emitter assemblies 82 include a vertical-cavity surface-emitting laser (VCSEL), an edge-emitting laser (EEL), and a light-emitting diode (LED). For emitter assemblies 82 that emit laser beams, the beams may be single mode or multimode.

Herein, the emitter assemblies 82, optical arrangements 84, image sensing modules 86, and beams 100 are identified collectively or generically by the respective reference characters 82, 84, 86, and 100 (e.g., "beam(s) 100") and individually by these reference characters followed by a letter suffix (e.g., "single solid beam 100a").

Figures 31, 32:
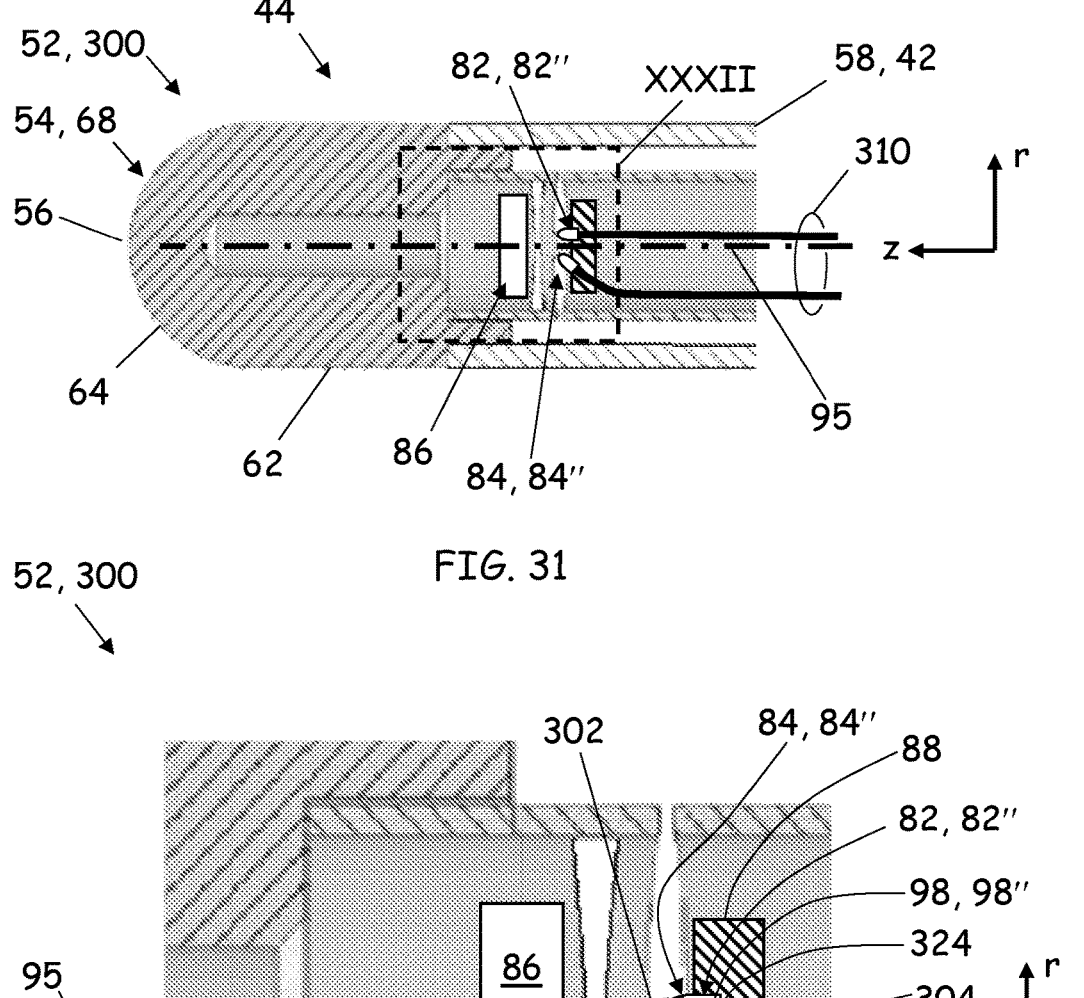
FIG. 31 is a sectional view of a distal end portion of a force sensing catheter utilizing a dual beam configuration according to an embodiment of the disclosure.
FIG. 32 is an enlarged view at inset XXXII of FIG. 31 according to an embodiment of the disclosure.

The emitter(s) 98 of the emitter assembly 82 may include a single emitter 98' (FIG. 5) or a plurality of distributed emitters 98" of prescribed position and orientation relative to each other (e.g., FIG. 32). The emitter assembly 82 may be mounted to either the proximal portion 92 or the distal portion 94 of the deformable body 60, with the image sensing module 86 being mounted to the opposed distal portion 94 or proximal portion 92. The emitter assembly 82 and image sensing module 86 may be physically at the same axial location as and surrounded by the respective portion 92, 94 to which it is mounted. Alternatively, one or both of the emitter assembly 82 and image sensing module 86 may be physically located at a location that is distal or proximal to the location of the respective portion 92, 94 to which it is mounted.

The embodiment of FIGS. 4 and 5 depict one possible arrangement for the force sensor assembly 52. The emitter assembly 82, the optical arrangement 84, the optical mount 88, and the image sensing module 86 may also be arranged in a different order, from distal to proximal or vice-versa. In the depicted embodiment, the emitter assembly 82 emits electromagnetic radiation in a proximal direction 106, from the distal portion 94 towards the proximal portion 92. In alternative embodiments, the emitter assembly 82 may emit electromagnetic radiation in a distal direction 108, from the proximal portion 92 towards the distal portion 94 (e.g., FIG. 31). In some embodiments, the emitter assembly 82 and optical arrangement 84 are distributed, thereby appearing as a plurality of components, such as depicted in FIG. 32.

Figures 27, 28, 29, 30:
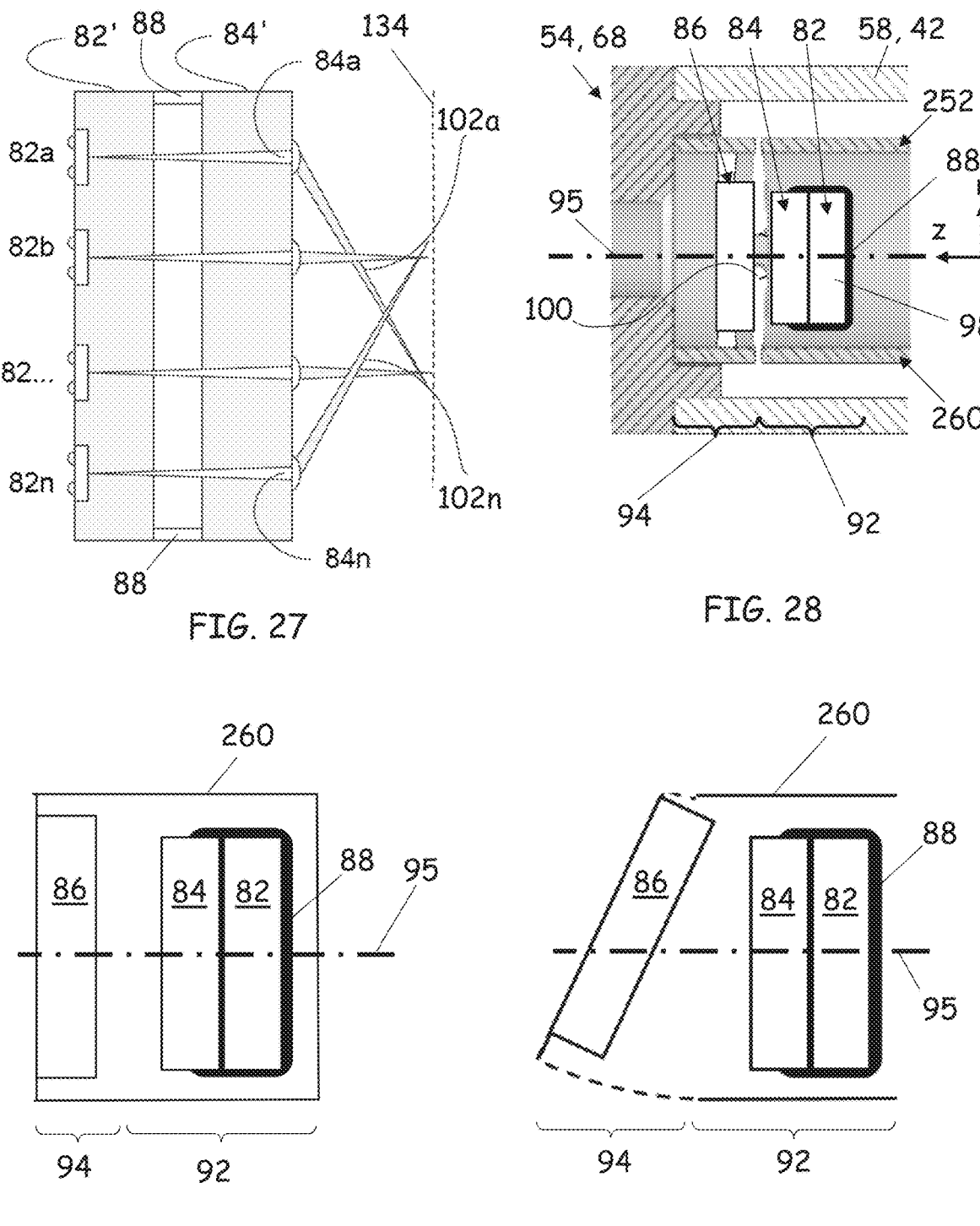
FIG. 27 is a schematic view of a unitary emitter assembly radiatively and physically coupled to a unitary optical arrangement according to an embodiment of the disclosure.
FIG. 28 is an enlarged sectional view of a modified configuration for a force sensor assembly according to an embodiment of the disclosure.
FIG. 29 is a schematic of the modified configuration of FIG. 28 in an unloaded state according to an embodiment of the disclosure.
FIG. 30 is a schematic of the modified configuration of FIG. 28 in a loaded state according to an embodiment of the disclosure.

The optical arrangement 84 is configured to receive electromagnetic radiation from the emitter assembly 82 for formation of the beam(s) 100 and convey the electromagnetic radiation to the image sensing module 86. The optical arrangement 84 is in a rigid and known relationship with the emitter assembly 82, and may be proximate thereto, or at a known distance thereto. In some embodiments, the optical arrangement 84 includes one or more DOEs (diffractive optical elements), lenses, apertures, prisms, diffractive elements, refractive elements, or a combination thereof. The optical arrangement 84 may be a unitary component 84' (FIG. 5) that includes one or more optical elements, such as beam splitting and focusing components (not depicted). Herein, a "unitary" component is a single optical component that includes all geometrical properties able to distribute electromagnetic radiation in an appropriate way (e.g., a DOE) coming from a single or distributed emitter assembly 82. An example of both a unitary emitter assembly 82' and a unitary optical arrangement 82' 84' is depicted at FIG. 27, schematically depicting a DOE.

Alternatively, the optical arrangement 84 may be a plurality of components 84" distributed among a plurality of components 82" of the emitter assembly 82 (e.g., FIG. 32). In some embodiments, optical components are integrated into the emitter assembly 82 such that there is no distinct or separate optical arrangement 84. The optical arrangement 84 may define a beam datum or datums 122 from which propagation of the beam(s) 100 is referenced the datum(s) 122 defining one or more designated planes 126 that represents a location from which formed beams 100 are propagated (e.g., FIGS. 32, 35). The reference plane(s) 126 are orthogonal to the central axis 95. For the single/integrated component 84', the beam datum 122 may be a planar face 124 of the optical arrangement 84 that opposes and faces the image sensing module 86 (FIG. 5).

The image sensing module 86 may include a 2D (two-dimensional) image sensor 132 that detects incident electromagnetic radiation, the 2D image sensor 132 defining a detection plane 134. Non-limiting examples of the 2D image sensor 132 include a CMOS (complementary metal oxide semiconductor) or a CCD (charged coupled device). The 2D image sensor 132 may be monochromatic or a multichromatic. The 2D image sensor 132 includes a 2D array of pixels 136 (FIG. 11) which may be characterized by a pixel density 138. The image sensing module 86 may be in communication with the control and signal processing system 78, for example, via signal wires that extend through the catheter shaft 42 and control handle 74 to the control and signal processing system 78.

Figures 7, 8, 9, 10, 11, 12:
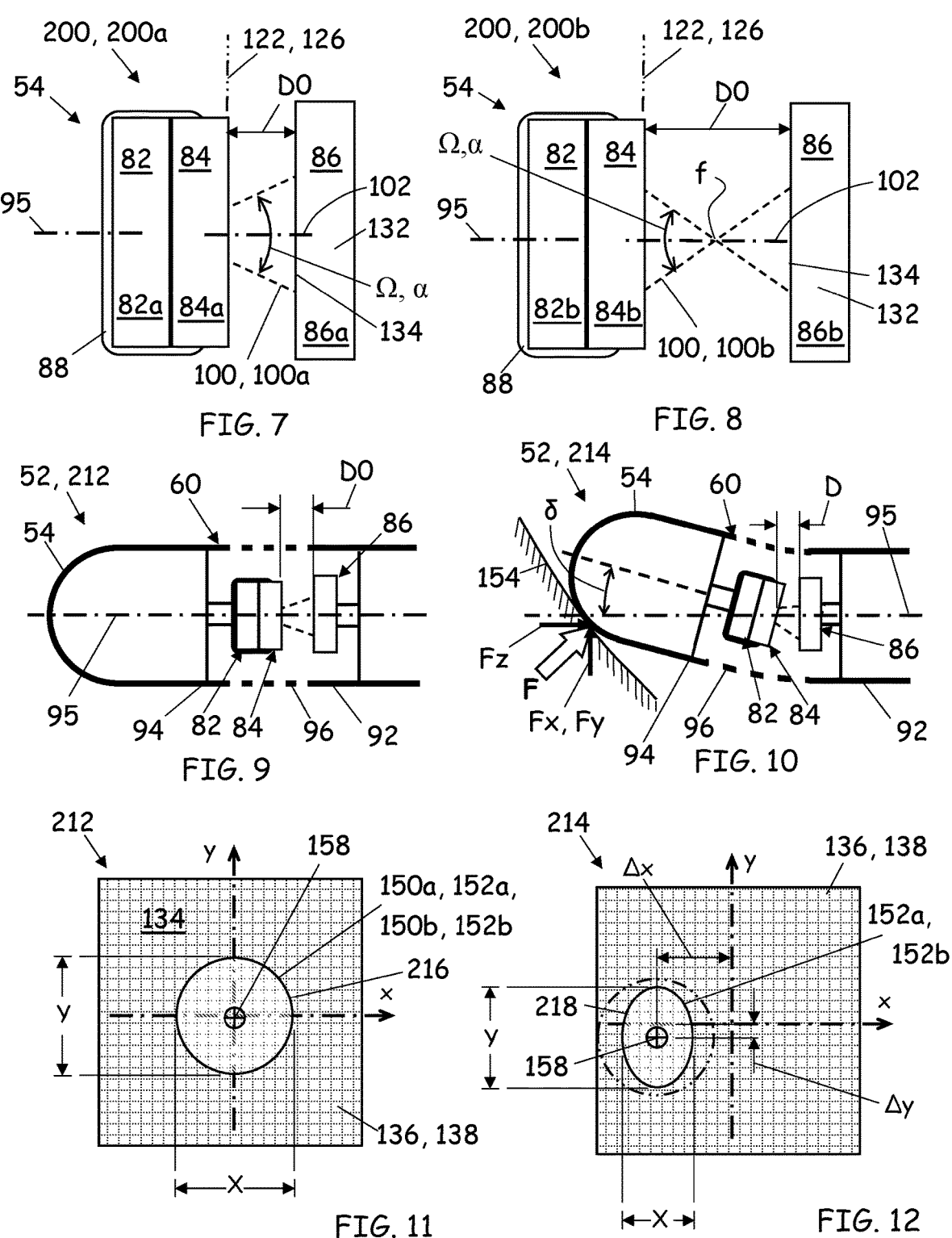
FIG. 7 is a schematic of a divergent beam configuration for a force sensing assembly according to an embodiment of the disclosure.
FIG. 8 is a schematic of a convergent beam configuration for a force sensing assembly according to an embodiment of the disclosure.
FIG. 9 is a schematic of a force sensor assembly utilizing the divergent beam configuration of FIG. 7 in an unloaded state according to an embodiment of the disclosure.
FIG. 10 is a schematic of the force sensor assembly of FIG. 9 in a loaded state according to an embodiment of the disclosure.
FIG. 11 is a plan view of an irradiation shape incident on the detection plane of the force sensor assembly as depicted in FIG. 9 according to an embodiment of the disclosure.
FIG. 12 is a plan view of an irradiation shape incident on the detection plane of the force sensor assembly as depicted in FIG. 10 according to an embodiment of the disclosure.

In assembly, the image sensing module 86 is mounted opposite the optical arrangement 84 and arranged to subtend the beam(s) 100 that exit the optical arrangement 84. The subtended beam(s) 100 define an irradiation pattern 150 at the detection plane 134 (FIG. 11). The force sensing assemblies 52 may be characterized by a baseline axial separation DO, defined as a distance between the detection plane 134 and the beam datum(s) 122 as measured parallel to the central axis 95 when the force sensor assembly 52 is in an unloaded state. In some embodiments, the baseline axial separation DO is in a range from 0.3 mm to 0.7 mm inclusive. In some embodiments, the baseline axial separation DO is in a range from 0.05 mm to 4 mm. In some embodiments, the baseline axial separation DO is in a range from 0.1 mm to 2 mm. In some embodiments, the baseline axial separation is nominally 0.5 mm.

The image sensing module 86 is physically coupled to the portion 94, 92 that opposes the portion 92, 94 to which the emitter assembly 82 is physically coupled. Accordingly, the image sensing module 86 is either positioned in the distal portion 94 to intercept radiation emitted distally from the emitter assembly 82 mounted to the proximal portion 92, or positioned in the proximal portion 92 to intercept radiation emitted in the proximal direction 106 from the emitter assembly 82 mounted to the distal portion 94. The image sensing module 86 may be physically located within and surrounded by the respective portion 92, 94 to which it is mounted. Alternatively the image sensing module 86 may be physically located or extend proximal to or distal to the respective portion 92, 94 to which it is mounted. For embodiments that include the compliant mid-portion 96, the beam(s) 100 may pass therethrough.

The optical mount 88 may comprise a metallic, polymer or other material which ensures the relative positioning and orientation of the various components affixed thereto. The optical mount 88 may be physically coupled to either the distal portion 94 or the proximal portion 92 of the deformable body 60, as described above. The optical mount 88 maintains the position and orientation of the components of the emitter assembly 82 and the optical arrangement 84, as well as the position and orientation of any distributed emitters 98" that are within the emitter assembly 82.

Functionally, the distal tip 54 applies a catheter force to the tissue of an endocardial wall 154, and is subjected to an equal and opposite reaction force F (FIG. 10). The smooth surface 65 of the distal tip 54 limits friction with the endocardial wall 154, such that the force may be considered normal to the surface of the distal tip 54. For distal tips 54 including the hemispherical end 64, and assuming frictionless contact between the endocardial wall 154 and the distal tip 54, the reaction force F exerted on the distal tip 54 may be assumed collinear with the origin of the radius of the hemispherical end 64 of the distal extremity 56.

The axial and lateral compliance of the deformable body 60 enables proximal and distal portions 92 and 94, as well as any component physically coupled therewith, to translate and rotate relative to one another under the effect of the reaction force F exerted by the endocardial wall 154 on the distal tip 54. Because of the compliance, the relative position and orientation between the image sensing module 86 and the combined emitter assembly 82 and the optical arrangement 84 changes in proportion to the reaction force F applied on the distal tip 54, causing the irradiation pattern 150 to shift and/or change size on the detection plane 134.

The optical arrangement 84 shapes the electromagnetic radiation emitted by the emitter assembly 82 to form the beam(s) 100 for delivery of desired irradiation shape(s) 152 on the detection plane 134 of the image sensing module 86. The optical arrangement 84 may project the electromagnetic radiation that passes therethrough to define, for example, a cone, a discrete number of parallel or non-parallel beams, or a combination thereof. The irradiation shape 152 may be of a variety of geometries, for example circular, elliptical, or oblong.

The image sensing module 86 resolves the irradiation pattern 150 incident on the detection plane 134 of the 2D image sensor 132. The irradiation shape(s) 152 of the irradiation pattern 150 defines an irradiation shape centroid 158 (FIG. 11), which identifies the location of the propagation axis 102 within the irradiation shape 152. In some embodiments, the image sensing module 86 has sufficient resolution for resolving a plurality of incident irradiation shapes 152. Resolution of the irradiation shape(s) 152 is determined by the pixel density 138. Higher pixel densities 138 (smaller pixel sizes) improve the resolution of the irradiation shape(s) 152 and may thereby improve the sensitivity to the reaction force F applied on the distal tip 54. In some embodiments, pixel sizes are in a range from 2.4 μm (micrometer) to 5 μm inclusive, with 2.4 μm being state of the art for current two-dimensional imaging devices. In some embodiments, pixel densities 138 may be in a range from 83 kpx (kilopixels) to 170 kpx per square mm.

Functionally, having the emitter assembly 82 and image sensing module 86 at the same axial location as the respective portion 92, 94 to which it is mounted enables a compact design of the force sensing assembly 52. On the other hand, embodiments where one or both of the emitter assembly 82 and image sensing module 86 is physically located at a location that is distal to or proximal to the location of the respective portion 92, 94 can enable more favorable arrangement of other components and attributes of the distal end portion 44. The ability to position the components of the force sensor assembly 52 also enables independent "tuning" of the sensitivity to axial the force component Fz and the lateral force components Fx and Fy.

Referring to FIG. 6, an example of such a more favorable arrangement is depicted according to an embodiment of the disclosure. Consider that the length of the respective standoff structure 162 can serve to amplify the effect of the dynamic deflection angle δ. As such, the sensitivity to dynamic lateral deflection can be tuned by implementation of the standoff structures 162, 164.

Consider also that the distal tip 54 of FIG. 6 is formed so that most of the cylindrical base 62 extends proximally into the deformable body 60. The optical mount 88 is physically coupled to the distal end portion 94 and the image sensing module 86 to the proximal portion 92 of the deformable body 60 with respective standoff structures 162, 164 that extends these components proximal to the deformable body 60. While this may lengthen the overall force sensing assembly 52, such an arrangement may prove useful for other aspects of the force sensing catheter 40, such as the routing of irrigation fluid and connection of power leads.

In operation, the force sensor assembly 52 relies on sensing a displacement of the distal portion 94 relative to the proximal portion 92, caused by axial translation and lateral flexing of the deformable body 60. This translation and flexing are caused by the reaction force F that imparts relative translational and rotational displacements of the distal portion 94 (and distal tip 54) relative to the proximal portion 92 of the deformable body 60. The reaction force F is sensed by and derived from the measurement of two-dimensional changes (size and/or displacement) of the irradiation pattern 150 on the detection plane 134 of the 2D image sensor 132.

The image sensing module 86 transmits signals corresponding to the irradiation pattern 150, for example signal amplitudes transmitted as a series of point (pixel) coordinates to the control and signal processing system 78 for processing. Communication between the image sensing module 86 and the control and signal processing system 78 may be analog or digital. The sensed changes in the position and size of the irradiation pattern 150 relative to an initial, unloaded state 212 enable resolution of the vectoral components of the reaction force vector F. The resolution of the reaction force vector F is accomplished by conventional techniques, such as calibration matrix inversion, calibration data reverse fitting, superposition, or other conventional calibration techniques known to the artisan. An example of such techniques is found at U.S. Patent Application Publication No. 2012/0265102 to Leo et al., the disclosure of which is hereby incorporated by reference herein in its entirety except for patent claims and express definitions contained therein. Example data sets and associated characteristics are outlined in general terms below.

Following are representative configurations 200 of force sensing assemblies 52 for sensing changes in the irradiation pattern 152 caused by deformation of the deformable body 60 under the influence of the reaction force F. The configurations 200, as well as configurations 300 attendant to FIGS. 31 through 44 below, are identified collectively or generically by the reference characters 200 and 300 (i.e., "configuration(s) 200") and individually by the reference character 200, 300 followed by a letter suffix (e.g., "divergent beam configuration 200a"). The various configurations 200, 300 may include some or all of the same components and attributes as the force sensor assembly 52 and as described for other of the configurations 200, 300, some of which are indicated with same-labeled reference characters. All configurations 200, 300 are depicted and described as including the emitter assembly 82, the optical arrangement 84 and the image sensing module 86. As noted previously, the emitter assembly 82 and the optical arrangement 84 can, in some embodiments, be an integrated unit.

Referring to FIG. 7, a divergent beam configuration 200a is depicted according to an embodiment of the disclosure. The divergent beam configuration 200a is characterized by a solid beam 100a that defines a solid angle Ω about the beam propagation axis 102. The solid angle Ω may be symmetrical, asymmetrical, or axisymmetric (mirrored) about the propagation axis 102. The divergent beam configuration 200a is so-named because the solid beam 100a diverges upon exiting the optical arrangement 84. A profile angle α is defined by the solid angle Ω. Herein, a "profile angle" is a two-dimensional angle that is co-planar with the beam propagation axis 102. Generally, for all configurations 200, the profile angle α may be within a range from 0 degrees (collimated) to 150 degrees inclusive. In some embodiments, the profile angle α may be within a range of 30 degrees to 150 degrees inclusive. In some embodiments, the profile angle α defines an acute angle.

Referring to FIG. 8, a convergent beam configuration 200b is depicted according to an embodiment of the disclosure. The convergent beam configuration 200b is characterized by a single solid beam 100b that defines the solid angle Ω about the beam propagation axis 102. The convergent beam configuration 200b is so-named because the single solid beam 100a converges upon exiting an optical arrangement 84b. In some embodiments, a focal point f of the beam 100b is within the baseline axial separation DO between the optical arrangement 84b and the image sensing module 86, such that the beam 100b is diverging when incident on the detection plane 134. Though not depicted, embodiments where the detector plane 134 intercepts the beam 100b before convergence at the focal point f is also contemplated.

In some embodiments, the irradiation pattern 150 is provided by a single convergent beam 100b.

The beam configurations 200a, 200b create irradiation shapes 152a, 152b where the beam 100a, 100b is subtended by the detection plane 134 of the image sensing module 86a, 86b (FIGS. 11 and 12). The irradiation shape 152 may be of a variety of geometries, for example circular, elliptical, or oblong. For both beam configurations 200a, 200b, the optical arrangements 84a, 84b shape and direct the electromagnetic radiation emitted from the emitter assembly 82a, 82b to form the desired profile angle α. The optical arrangements 84a, 84b may also direct the beam at a desired incidence angle γ of the propagation axis 102 relative to a normal vector N of the detection plane 134 when in the unloaded state 212 (e.g., FIG. 13).

Functionally, in addition to the compliance of the deformable body 60, the sensitivity of the configuration to the applied force depends on the profile angle α, and the baseline axial separation D0. The divergence of the profile angle α at the image sensing modules 86a, 86b enables the irradiation shapes 152a, 152b to change size in response to changes in the axial force component Fz of the reaction force vector F. The divergent beam configuration 200a may provide this aspect in a compact design for the force sensor assembly 52. For the convergent beam configuration 200b, the convergence of the beam 100b for the convergent beam configuration 152b enables the baseline axial separation D0 to be increased without an increase of the overall dimensions of the irradiation shapes 152b. The increased baseline axial separation D0 causes greater lateral movement of the irradiation shape 152b on the detection plane 134 for a given lateral displacement of the distal tip 54, without necessarily requiring an attendant increase in the dimensions of the 2D image sensor 132. By this arrangement, the sensitivity of the convergent beam configuration 200b may be enhanced while remaining within dimensional constraints required of the force sensing catheter 40.

Referring to FIGS. 9 through 12, principles of operation for the beam configurations 200a, 200b are depicted according to an embodiment of the disclosure. FIGS. 9 and 11 are representative of the force sensor assembly 52 in an unloaded state 212, whereas FIGS. 10 and 12 are representative of the force sensor assembly 52 in a loaded state 214. An outline of the irradiation shape 152a, 152b in the unloaded state 212 of FIG. 11 is depicted in phantom in FIG. 12, but concentric with the irradiation shape centroid 158 of the loaded state 214, for illustration of certain dynamic parameters as described below.

The force sensor assembly 52 is tared in the unloaded state 212. The propagation axis 102 (i.e., irradiation shape centroid 158) may be substantially centered on the detection plane 134. In the unloaded state 212, the irradiation shapes 152a, 152b for the beam configurations 200a, 200b may define a substantially circular geometry 216 about the propagation axis 102, thereby defining a dimension X (dimension parallel to the x-axis) and a Y dimension (dimension that is parallel to the y-axis) of the irradiation shape 152a, 152b that are substantially equal. Herein, "substantially" as related to the various parameters of the irradiation shapes 152 is defined as being within an uncertainty of the associated parameter as measured by the force sensor assembly 52.

Figures 13, 14, 15, 16, 17, 18:
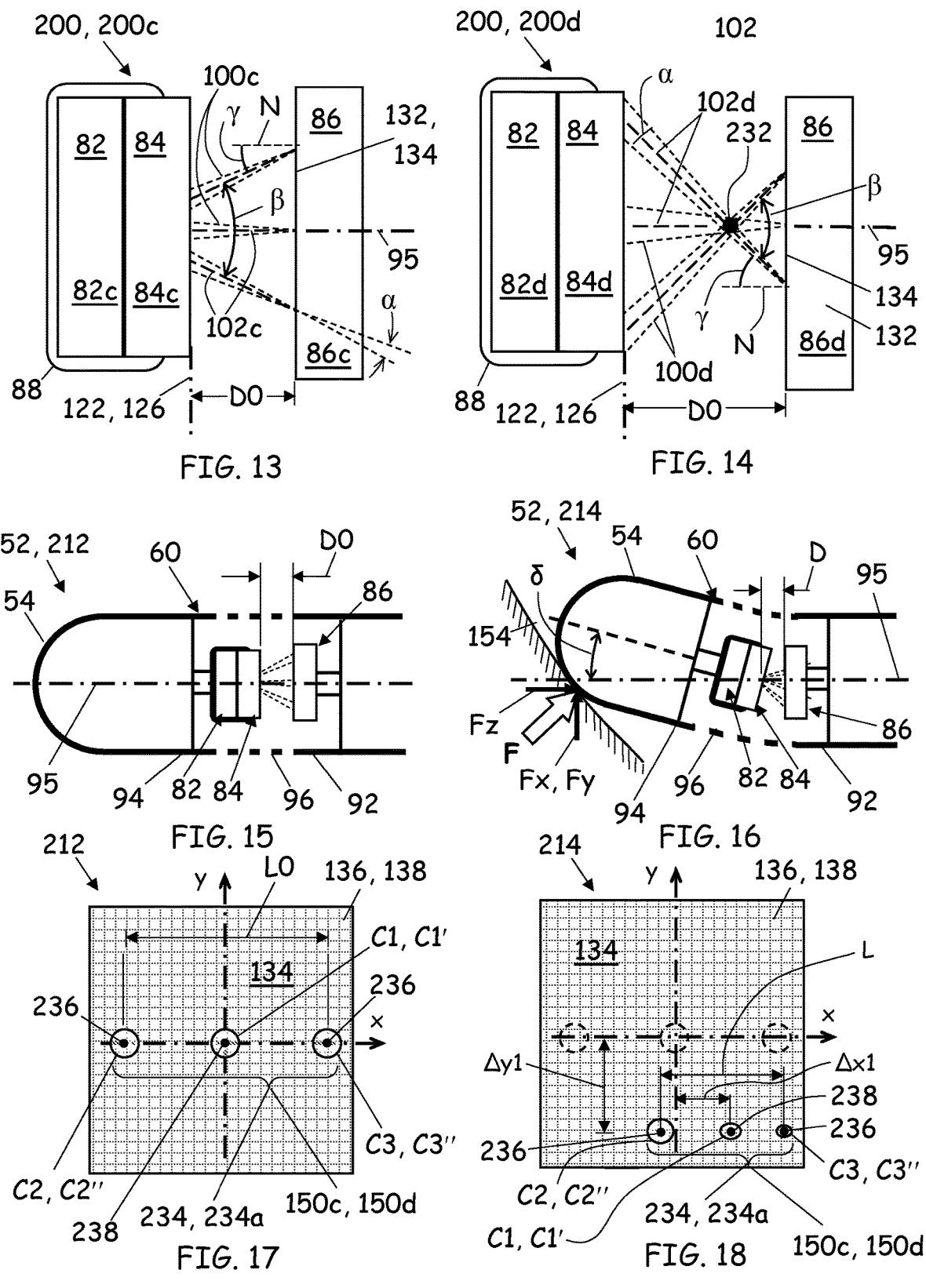
FIG. 13 is a schematic of a multiple divergent beam configuration for a force sensing assembly according to an embodiment of the disclosure.
FIG. 14 is a schematic of the multiple convergent beam configuration for a force sensing assembly according to an embodiment of the disclosure.
FIG. 15 is a schematic of a force sensor assembly in an unloaded state and utilizing the multiple divergent beam configuration of FIG. 13 according to an embodiment of the disclosure.
FIG. 16 is a schematic of the force sensor assembly of FIG. 15 in a loaded state according to an embodiment of the disclosure.
FIG. 17 is a plan view of an irradiation pattern incident on a detection plane of the force sensor assembly as depicted in FIG. 15 according to an embodiment of the disclosure.
FIG. 18 is a plan view of the irradiation pattern incident on a detection plane of the force sensor assembly as depicted in FIG. 16 according to an embodiment of the disclosure.
Figures 19, 20:
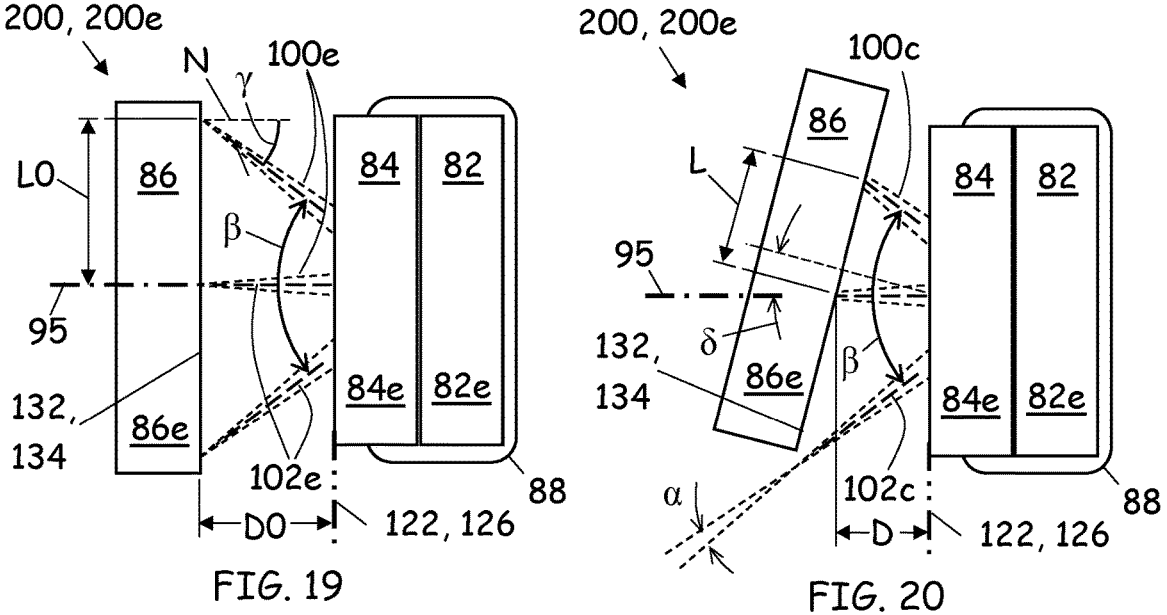
FIGS. 19 and 20 are schematic views of the operation of a force sensor assembly configured for enhanced sensitivity according to an embodiment of the disclosure.
Figures 21, 22:
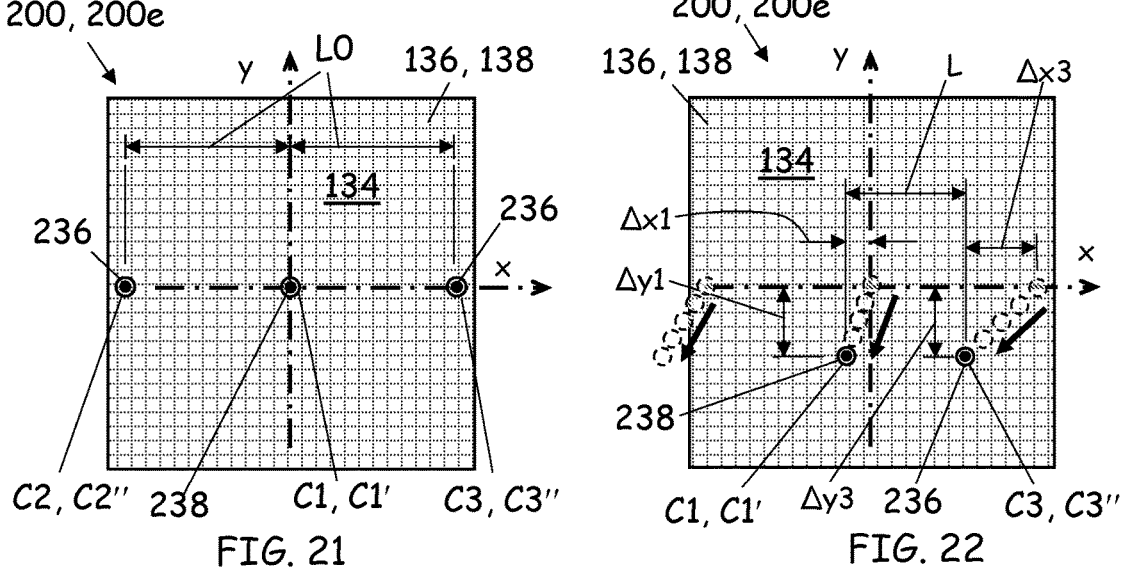
FIGS. 21 and 22 are plan views of an irradiation pattern incident on the detection plane of the force sensor assembly corresponding to FIGS. 19 and 20, respectively, according to an embodiment of the disclosure.

The irradiation patterns 150 depicted herein, particularly for the unloaded state 212, are idealized representations, wherein the irradiation pattern 150 is centered on the detection plane 134, the sizes of the irradiation shapes 152 (as well as Cj discussed attendant to FIGS. 17, 25, 41 and 43) are well defined, and the arrangement 234 is perfect (linear in the case of FIG. 17). In practice, the artisan understands that such idealized aspects of the irradiation pattern 150 is for illustration only, and non-limiting.

In the loaded state 214, the distal tip 54 of the force sensor assembly 52 is brought into contact with the endocardial wall 154. The axial force component Fz causes the distal portion 94 of the deformable body 60 to move toward the proximal portion 92, thereby causing the image sensing module 86 and the optical arrangement 84 to move closer together. This movement is characterized by a dynamic axial separation D, defined as a distance between the detection plane 134 and the beam datum(s) 122 as measured parallel to the central axis 95 when the force sensor assembly 52 is in the loaded state 214. In the depicted embodiment, the dynamic axial separation D is less than the baseline separation D0.

Lateral bending of the deformable body a dynamic deflection angle δ relative to the central axis 95. Movement of the distal portion 94 toward or away from the proximal portion 92 causes a dynamic change DX and/or DY (not depicted) of the dimension(s) X and/or Y, where DX and DY are, respectively, the difference between the dimension X in the unloaded and loaded states 212, 214, and the difference between the dimension Y in the unloaded and loaded states 212, 214. The irradiation shape 152a, 152b causes the irradiation shape centroid 158 to move laterally on the detection plane 134. The lateral movement of the irradiation shape centroid 158 may be characterized by dynamic distances Δx and Δy, which are the distances that the irradiation shape centroid 158 displaced in the x- and y-directions, respectively, relative to the location of the irradiation shape centroid 158 in the unloaded state 212.

For the configurations 200a and 200b, the lateral components Fx and Fy of the reaction force F imposed on the distal tip 54 predominantly influences the positional displacement (dynamic distances Δx and Δy) of the irradiation shape centroid 158, while the axial component of the force Fz predominantly influences the change of the dimension(s) X and/or Y of the irradiation shape(s) 152. However, all parameters of the irradiation shape(s) 152 may be dependent to some extent on all of the force vector components. For example, a secondary effect of a non-zero dynamic deflection angle δ is a dynamic change DX and/or DY of the dimension(s) X and/or Y. The dynamic changes DX and DY caused by the lateral force component(s) Fx and/or Fy may be unequal, causing a difference between the dynamic changes DX and DY. The differences between the dynamic changes DX and DY may cause the circular geometry 216 of irradiation shape(s) 152 in the unloaded state 212 to change into an elliptical geometry 218 in the loaded state 214 (depicted).

The irradiation pattern 150 may be characterized by a set of scalar values Si. The scalar values Si may represent some or all of the various dimensions and dynamic parameters corresponding to changes in the irradiation shape 152a, 152b, as well as irradiation patterns 150 generally. These dimensions and dynamic parameters include, but are not limited to, the dimensions X and Y, the dynamic distances Δx and Δy, the dynamic changes DX and DY. Other scalar values Si that may be provided by the irradiation shape 152 includes a ratio of the dimensions X and Y, an ellipse radii, surface area, or circumference of the irradiation shape 152, as well as dynamic changes thereto. Determination of such dimensions and dynamic parameters may be performed, for example, by the control and signal processing system 78.

The scalar values Si may be represented by a scalar array A $$A = \begin{pmatrix} S1 \\ S2 \\ ... \\ Sn \end{pmatrix} \qquad \text{Eq. (1)}$$

where Si are the scalar values for (i=1 . . . n). For resolution of force in three-dimensional space, n is equal to or greater than three. Herein, scalar arrays are referred to generically and collectively as with reference character A (e.g., "scalar array(s) A") and specifically or individually by reference character A followed by a letter suffix (e.g., "unloaded scalar array AU").

For the beam configurations 200a, 200b, an unloaded scalar array AU may be determined and recorded with the force sensor assembly 52 in an unloaded (baseline) state:

$$AU = \begin{pmatrix} S1,0 \\ S2,0 \\ ... \\ Sn,0 \end{pmatrix} \qquad \text{Eq. (2)}$$

where Si,0 is the respective scalar value for characterizing the two-dimensional irradiation shape 152 for (i=1 . . . n). A loaded scalar array AL may be determined and recorded with the force sensor assembly 52 in a loaded (dynamic) state:

$$AL = \begin{pmatrix} S1,0 + \Delta S1 \\ S2,0 + \Delta S2 \\ ... \\ Sn,0 + \Delta Sn \end{pmatrix} \qquad \text{Eq. (3)}$$

where $\Delta Si$ is a change in the respective scalar value Si relative to the baseline state.

In some embodiments, a linear variation of the force may induce a linear variation of the scalars Si. Accordingly, the values of the scalar array A, or functions thereof, can be linked by conventional calibration techniques wherein a relationship between sensed changes in the irradiation pattern (or vector components directly) and a known force vector applied at the distal tip 54 is established. Examples include calibration matrix inversion, function fitting, superposition, and other conventional calibration techniques known to the artisan.

Referring to FIG. 13, a multiple divergent beam configuration 200c is depicted according to an embodiment of the disclosure. The divergent multiple beam configuration 200c uses a discrete number m of beams 100c, with m being greater than or equal to two and each defining a corresponding solid angle $\Omega$ and profile angle $\alpha$. The beams 100d propagate along a respective propagation axis 102 to intersect the detection plane 134. The multiple beams 100c intersect the detection plane 134 at corresponding incidence angles $\gamma$ relative to a normal vector N, the incidence angles $\gamma$ being defined when the force sensor assembly 52 is in the unloaded state 212. The multiple divergent beam configuration 200c is so-named because the propagation axes 102c are directed in a divergent manner upon exiting the optical arrangement 84c. A maximum open angle $\theta$ is defined between the propagation axes 102c of two of the beams 100c.

Referring to FIG. 14, a multiple convergent beam configuration 200d is depicted according to an embodiment of the disclosure. Multiple beams 100d of the multiple convergent beam configuration 200d may have the same or similar characteristics as described for the multiple divergent beam configuration 200c. The multiple convergent beam configuration 200d is so-named because the propagation axes 102d are directed in a convergent manner upon exiting the optical arrangement 84d. A distinction of the multiple convergent beam configuration 200d is that the two of the multiple propagation axes 102 and/or multiple beams 100c cross over at an intersection 232 to define the maximum open angle $\beta$. Though not depicted, embodiments where the detector plane 134 intercepts the multiple beams 100d before intersection is also contemplated.

The multiple beam configurations 200c, 200d create respective irradiation patterns 150c, 150d that comprise a plurality of irradiation spots C. Individual irradiation spots of the plurality of irradiation spots C are identified as irradiation spots Cj, where j is an integer greater than or equal to two. For example, FIGS. 17 and 18 each depict three such irradiation spots Cj, distinguished from each other as irradiation spots C1, C2, and C3. The irradiation patterns 150c, 150d may be characterized by an arrangement 234 of the irradiation spots Cj with respect to each other. For example, the arrangement 234 of the irradiation spots C1, C2, and C3 of FIGS. 17 and 18 can be described as a linear arrangement 234a. Other arrangements 234 are also contemplated, such as outlining a cross pattern, the corners or outline of a polygon, or a circle. Examples of DOEs that generate such patterns are conventionally available, for example from Zhongshan He Tong Optics Electronic Technology Co., Ltd. of Tainan City, Taiwan (R.O.C), examples of which are available at http://www.htgdlaser.com/node-135_lang,en, last visited Apr. 5, 2021.

Herein, an "irradiation spot" Cj is a small irradiation shape 152, distinguished from irradiation shapes 152 generally by one or both of the profile angle $\alpha$ and/or a maximum dimension. In some embodiments, an irradiation spot Cj is defined by a profile angle $\alpha$ that is in a range from 0 degrees (collimated) to five degrees inclusive for the associated beam 100; in some embodiments, the profile angle $\alpha$ is in a range from 0.5 degree to three degrees inclusive; in some embodiments the profile angle $\alpha$ is in a range from one degree to two degrees inclusive. For data verification, the irradiation spots Cj should be large enough to cover more than one pixel, but small enough for legitimate approximation of location without resorting to area centroid calculation. Accordingly, alternatively or in addition, irradiation spots Cj may be characterized as irradiating a maximum number of pixels that is in a range from two to 10 pixels inclusive; in some embodiments, in a range from two to six pixels inclusive; in some embodiments, from two to four pixels inclusive. Dimensionally, for a state-of-the-art pixel size of 2.4 µm, a maximum dimension that is in a range from three to 25 µm inclusive; in some embodiments, in a range from three to 15 µm inclusive; in some embodiments, in a range from three to 10 µm inclusive.

For the multiple beam configurations 200c, 200d, the optical arrangements 84c, 84d shape and direct the electromagnetic radiation emitted from the emitter assembly 82a, 82b to form desired characteristics of the irradiation pattern 150c, 150d, including but not limited to the profile angles $\alpha$, the incidence angles $\gamma$, the maximum open angle $\beta$, and the size and arrangement 234 of the irradiation spots Cj. In some embodiments, the optical arrangements 84c, 84d may include a DOE or a dedicated optical sub-assembly (for example, beam splitters and focus lenses) to create the desired irradiation patterns 150c, 150d. The emitter assemblies 82c, 82d and optical arrangements 84c, 84d may be unitary components (depicted) or distributed components. Examples of distributed components for the emitter assemblies 82 and optical arrangements 84 are presented below attendant to FIGS. 31 through 38.

Functionally, the multiple beam configurations 200c, 200d may be used to determining the axial force component Fz without resort to characterizing sizes of irradiation shapes 152 or spots Cj. The open angle θ causes the associated irradiation spots Cj to move laterally on the detection plane 134 in response to the axial displacement of the distal portion 94 of the deformable body 60. Accordingly, identification of the respective irradiation spots Cj may be by paired coordinates (xj, yj). The use of smaller sized irradiation spots Cj characterized by position only reduces the impact of border effects, irradiation shape geometry, and radiation intensity measurements associated with size changes of the irradiation shapes 152.

For example, determining the centroid of larger irradiation shapes 152 may rely on some form of averaging or area weighting of the intensity of the irradiation shape, and/or determining the location of the edge of the irradiation pattern. Both these requirements are subject to "border effects" of the detection plane 134, wherein pixels located near the borders of the detection plane 134 experience reduced or erratic sensitivity due to manufacturing limitations. In any case, the characterizing larger irradiation shapes 152 requires the shapes 152 to be totally subtended by the detection plane 134. This limits the range of motion on the detection plane 134, and is in conflict with the concept of using larger irradiation shapes 152 for greater sensitivity.

The multiple divergent beam configuration 200c may provide such functionality in a compact design for the force sensor assembly 52. On the other hand, the multiple convergent beam configuration 200d may provide enhanced sensitivity to the lateral shifting of the irradiation spots Cj. Another aspect of the multiple convergent beam configuration 200d is that the convergence of the beam 100d for the multiple convergent beam configuration 152d enables the baseline axial separation D0 to be increased without an increase of the overall dimensions of the irradiation pattern 150d. The increased baseline axial separation D0 causes greater lateral movement of the irradiation pattern 150d on the detection plane 134 for a given lateral deflection δ of the distal tip 54, without necessarily requiring an attendant increase in the dimensions of the 2D image sensor 132. By this arrangement, the sensitivity of the convergent beam configuration 200d may be enhanced while remaining within required dimensional constraints of the force sensing catheter 40. The longer axial separation distance D0 also provides greater clearance between components to avoid collision between the optical arrangement 84 and the image sensing module 86 during operation Referring to FIGS. 15 through 18, principles of operation for the multiple beam configurations 200c, 200d are depicted according to an embodiment of the disclosure. FIGS. 14 and 16 are representative of the force sensor assembly 52 in the unloaded state 212, whereas FIGS. 16 and 18 are representative of the force sensor assembly 52 in the loaded state 214. An outline of the irradiation pattern 150c, 150d in the unloaded state 212 of FIG. 17 is depicted in phantom in FIG. 18 for illustration of certain dynamic parameters as described below.

Each of the irradiation spots Cj may be characterized by a respective irradiation spot centroid 236, as sensed by the image sensing module 86c, 86d, that establishes a location of the corresponding irradiation spot Cj with paired coordinates (xj, yj). In some embodiments, the size of the irradiation spot Cj is made small relative to the resolution (pixel density) of the detection by tuning the baseline axial separation D0 so as to position the focal point of the beams 100c, 100d at the detection plane 134. Also, a profile angle α can maintain the small size of the irradiation spot Cj as the dynamic axial separation D changes. In such configurations, the irradiation spot centroids 236 may be approximated by local maxima signals from the array of pixels 136.

In some embodiments, a designated irradiation spot Cj' identifies a dynamic location 238 of the irradiation pattern 150c, 150d. In the depicted embodiment, the designated irradiation spot Cj' is irradiation spot C1 (labeled C1'), and the dynamic location 238 is associated therewith (FIGS. 17 and 18). Also, the dynamic location 238 may be substantially centered with the irradiation pattern 150c, 150d, and, in the unloaded state 212, may be substantially centered on the detection plane 134. Though irradiation spot C1 of FIGS. 17 and 18 represents both of these attributes, neither attribute is necessary for operation of the multiple beam configuration 200c, 200d.

Recall that two of the beams 100c, 100d define the maximum open angle β, herein referred to as β-defining beams, and the associated irradiation spots Cj referred to as β-defining irradiation spots Cj". A baseline lateral separation L0 is defined between the irradiation spot centroids 236 of the β-defining irradiation spots Cj" when in the unloaded state 212. A dynamic lateral separation L is defined between the irradiation spot centroids 236 of the β-defining irradiation spots Cj" when in the loaded state 214. The β-defining irradiation spots Cj" are irradiation spots C2 and C3 in FIGS. 17 and 18 (labeled as C2" and C3"), and the lateral separations L0, L are depicted therebetween.

The designated irradiation spot Cj' tracks across the detection plane 134 in response to the dynamic deflection angle δ to define a location change (Δxj, Δyj) of the designated irradiation spot Cj'. The dynamic deflection angle δ is caused by non-zero lateral force components Fx and Fy of the reaction force vector F. Accordingly, the lateral force components Fx and Fy may be determined primarily based on the location change (Δxj, Δyj) of the designated irradiation spot Cj'. This effect is illustrated FIG. 18 as the positional change (Δx1, Δy1) of the irradiation spot C1'.

The lateral separation L between β-defining irradiation spots Cj" changes with the dynamic axial separation D, by virtue of the angular separation of the open angle θ. That is, for movement between the optical arrangement 84c, 84d and the image sensing module 86c, 86d along the z-axis, the detection plane 134 subtends the open angle θ over a shorter or longer distance relative to the baseline axial separation D0, causing the irradiation spot centroids 236 to move closer together or further apart, respectively, which causes a change in the dynamic lateral separation L. Accordingly, the axial force component Fz may be inferred from a lateral separation change ΔL, defined as a difference between the dynamic lateral separation L and the baseline lateral separation L0. The open angle θ and the baseline axial separation D0 may be tuned to cover the range of axial force components Fz anticipated for a given application.

In some embodiments, as with irradiation shapes 152 of the beam configurations 200a, 200b, the individual irradiation spots Cj of the multiple beams 100c, 100d may define a variety of geometries, for example circular, elliptical, or oblong. Also, as with the beam configurations 200a, 200b, all parameters of the irradiation patterns 150 and shapes 152 may be dependent to some degree on all of the force vector components Fx, Fy, and Fz. Such secondary effects may include some dynamic changes DX and/or DY of the dimension(s) X and/or Y of each of the individual irradiation spots Cj of the irradiation patterns 150c, 150d.

Referring to FIGS. 19 through 22, a multiple beam configuration 200e is depicted according to an embodiment of the disclosure. The β-defining beams are arranged to be incident on the detection plane 134 at a broad open angle β, such that the corresponding β-defining irradiation spots C2" and C3" are proximate to the edges of the detection plane 134. The sensitivity of the force sensor assembly 52 to the axial force component Fz, being proportional to the open angle β, is thus enhanced for the multiple beam configuration 200e. For the multiple beam configuration 200e, the lateral separation L0 is not measured between the β-defining beams, but instead from the center beam corresponding to irradiation spot C1.

Upon application of a multi-component reaction force F, the distal section 94 may be laterally and axially displaced, as described for other multiple beam configurations 200 (e.g., FIGS. 15 and 16). In some load conditions, because of the proximity to the edge of the detection plane 134, one of the β-defining irradiation spots Cj" (irradiation spot C2" in FIG. 21) traces off the detection plane 134. This leaves only the other irradiation spots Cj (C1' and C2" in FIG. 22) incident on the detection plane 134. However, detection of the remaining irradiation spots Cj provides enough information to resolve the reaction force vector F in three dimensions.

In some embodiments, the energy source 76, emitter assembly 82, and/or optical arrangement is 84 is configured for selectively controlling the radiative coupling of one or more of the plurality of beams 100 of multiple beam configurations 200c-200f. The selective coupling may be controlled to apply to individual beams 100 or simultaneously to a subset of the individual beams 100. In some embodiments, the selective radiative coupling is provided by control of the energy source 76. That is, the energy source 76 may be configured to channel energy to individual beams 100, for example by electrical switching to individual local emitters 98 or interruption of the electromagnetic radiation supplied to individual channels of emitter assembly 82 via the fiber optic link 310. In some embodiments, the on/off switching of the radiative coupling(s) is controlled at a rate that is in a range of one Hz (Hertz) to 10 Hz inclusive. In some embodiments, the selective radiative coupling is controlled by the control and processing system 78.

Functionally, the ability to selectively control the radiative coupling of individual beams 100 enables confirmation of the source of the various irradiation spots Cj. Consider, for example, configuration 200d (FIG. 14). In some situations, the axial translation of the distal portion 94 of the deformable body 60 relative to the proximal portion 92 may cause the dynamic axial separation D to shorten such that detection plane 134 is temporarily located closer to the optical arrangement 84 than is the intersection point 238. For symmetrical irradiation patterns 152, one may not be able to discern the location of the plane (and there for the reaction force F) based on the irradiation pattern alone. Selective radiative coupling enables a given individual beams 100 to be switched off. The radiative decoupling can provide positive identification of the beam 100, from which the location of the intersection point 238 can be inferred. In a similar manner, the selective radiative coupling of individual beams 100 enables one to determine whether a given irradiation spot Cj is sourced from a given auxiliary beam 100f (configuration 200f at FIGS. 19 and 20).

Referring to FIGS. 23 through 25, a multiple beam configuration 200f is depicted according to an embodiment of the disclosure. As with multiple beam configuration 200e, the β-defining irradiation spots C2" and C3" are proximate the edges of the detection plane 134, and the lateral separation L0 is referenced from the center beam corresponding to irradiation spot C1. In addition, auxiliary beams 100f are propagated that are not incident on the detection plane 134 when in the unloaded state 212. Rather, the auxiliary beams 100f closely miss the detection plane 134 in the unloaded state 212.

As with the multiple beam configuration 200e, the β-defining irradiation spot C2" traces off the detection plane 134 upon application of the multi-component reaction force F. However, as the irradiation C2" traces off the detection plane 134, one of the auxiliary beams 100f becomes incident on the detection plane 134. Accordingly, there is always a sufficient number of beams incident on the detection plane 134 for detection and processing, as each beam provides two scalar values, thus providing the requisite minimum of three scalars for resolution of the reaction force vector F into the three components Fx, Fy, and Fz.

An increase in the number of beams, as well as an increase in the number of sensed parameters that change dynamically, can be utilized for redundancy and averaging or processing of the irradiation pattern 150, for example, to improve sensitivity and/or signal-to-noise ratios. For the multiple beam configurations 200c, 200d, the unloaded scalar array AU may be determined and recorded with the force sensor assembly 52 in the unloaded state 212:

$$AU = \begin{pmatrix} S1 = x1, 0; y1, 0 \\ S2 = x2, 0; y2, 0 \\ ... \\ Sm = xm, 0; ym, 0 \end{pmatrix} \qquad \text{Eq. (4)}$$

where the scalar values Sj are equal to the paired coordinates xj,0; yj,0 of the respective irradiation spot Cj in the unloaded (baseline) state 212 and m is the number of such paired coordinates. The loaded scalar array AL may be determined and recorded with the force sensor assembly 52 in the loaded state 214:

$$AL = \begin{pmatrix} S1' = x1; y1 \\ S2' = x2; y2 \\ ... \\ Sm' = xm; ym \end{pmatrix} \qquad \text{Eq. (5)}$$

where the scalar values Sj' are equal to the paired coordinates xj; yj of the respective irradiation spot Cj in the loaded (dynamic) state 212. In some embodiments, a linear variation of the force may induce a linear variation of the scalars Sj and Sj'. As such, the values of the scalar array A, or functions thereof, can be linked by conventional calibration techniques wherein a relationship between changes in the irradiation pattern 150 (or vector components directly) and a known force vector applied at the distal tip 54. Examples include calibration matrix inversion, function fitting, superposition, and other conventional calibration techniques known to the artisan.

Referring to FIGS. 28 through 30, a modified force sensor assembly 252 is depicted according to an embodiment of the disclosure. The modified force sensor assembly 252 includes some of the same components and attributes as the force sensor assembly 52, some of which are indicated by same-labeled reference characters. The modified force sensor assembly 252 is distinguished from the force sensor assembly 52 by an absence of a distinct mid-portion. That is, a modified deformable body 260 of the modified force sensor assembly 252 does not include the compliant mid-portion 96 of the force sensor assembly 52. Instead, the distal portion 94 and/or proximal portion 92 of the modified deformable body 260 are configured for sufficient compliance to enable relative axial translation and lateral flexing motion therebetween. The absence of a compliant mid-portion for the modified force sensor assembly 252 enables a more compact design relative to the force sensor assembly sensor 52. Any of the beam configurations 200 disclosed herein can be configured using the modified force sensor assembly 252.

Referring to FIGS. 31 and 32, implementation of a dual beam configuration 300 of the force sensor assembly 52 is depicted according to embodiments of the disclosure. The dual beam configuration 300 includes some of the same components and attributes as the multiple beam configurations 200c and 200d, some of which are identified with same-labeled reference characters. There are, however, several distinctions of the dual beam configurations 300 over the multiple beam configurations 200c, 200d, discussed below.

The dual beam configuration 300 may be characterized by two beams 302 and 303 delivered by two corresponding optical fibers 304 and 306. The dual beam configuration 300 implements the distributed forms 82" and 84" of the emitter assembly 82 and optical arrangement 84, wherein the optical arrangement 84 includes optical arrangement components 318 that are distributed amongst and physically and/or radiatively coupled to the respective optical fibers 304 and 306. The designated plane 126 is coplanar with the beam datum(s) 122, representing a location from which the formed beams 302 and 303 originate and from which the baseline and dynamic axial separations D0 and D are determined. In some embodiments, the beam 302 is substantially perpendicular to the detection plane 134 of the image sensing module 86 when the force sensor assembly 52 is in the unloaded state 212.

The beam 303 may be is referred to as a "canted" beam 303', with the corresponding propagation axis 102 being canted relative to the normal vector N of the detection plane 134, thereby defining the incidence angle γ when the force sensor assembly 52 is in the unloaded state 212. Incidence angles γ greater than 45 degrees act as an amplifier of axial movement, wherein lateral translation on the detection plane 134 is greater than the axial movement along the central axis 95. As the incidence angle γ approaches 90 degrees, the major axis of the elliptical shape 218 of the irradiation shape 352b approaches infinity and becomes subject to excessive elliptical deformation. Accordingly, in some embodiments, the incidence angle γ is in a range from 45 degrees to 85 degrees inclusive. In some embodiments, the incidence angle γ is in a range from 60 degrees to 70 degrees inclusive.

The depiction of the dual beam configuration 300 also provides an example of the image sensing module 86 being physically coupled to the distal portion 94 and the emitter assembly 82 and optical arrangement 84 being physically coupled to the proximal portion 92. This aspect, as explained above, is non-limiting.

In some of the dual beam configurations 300, the electromagnetic radiation for the emitter assembly 82 is remotely sourced and conveyed from the energy source 76 to the emitter assembly 82 via an optical fiber link 310, the energy source 76 being an electromagnetic emission source. The skilled artisan understands that the optical fiber link 310 is not limited to the dual beam configurations, and may in view of the teachings of this disclosure, incorporate optical fiber forms into the single- and multiple-beam configurations 200a-200d.

Figures 33, 34, 35, 36, 37, 38:
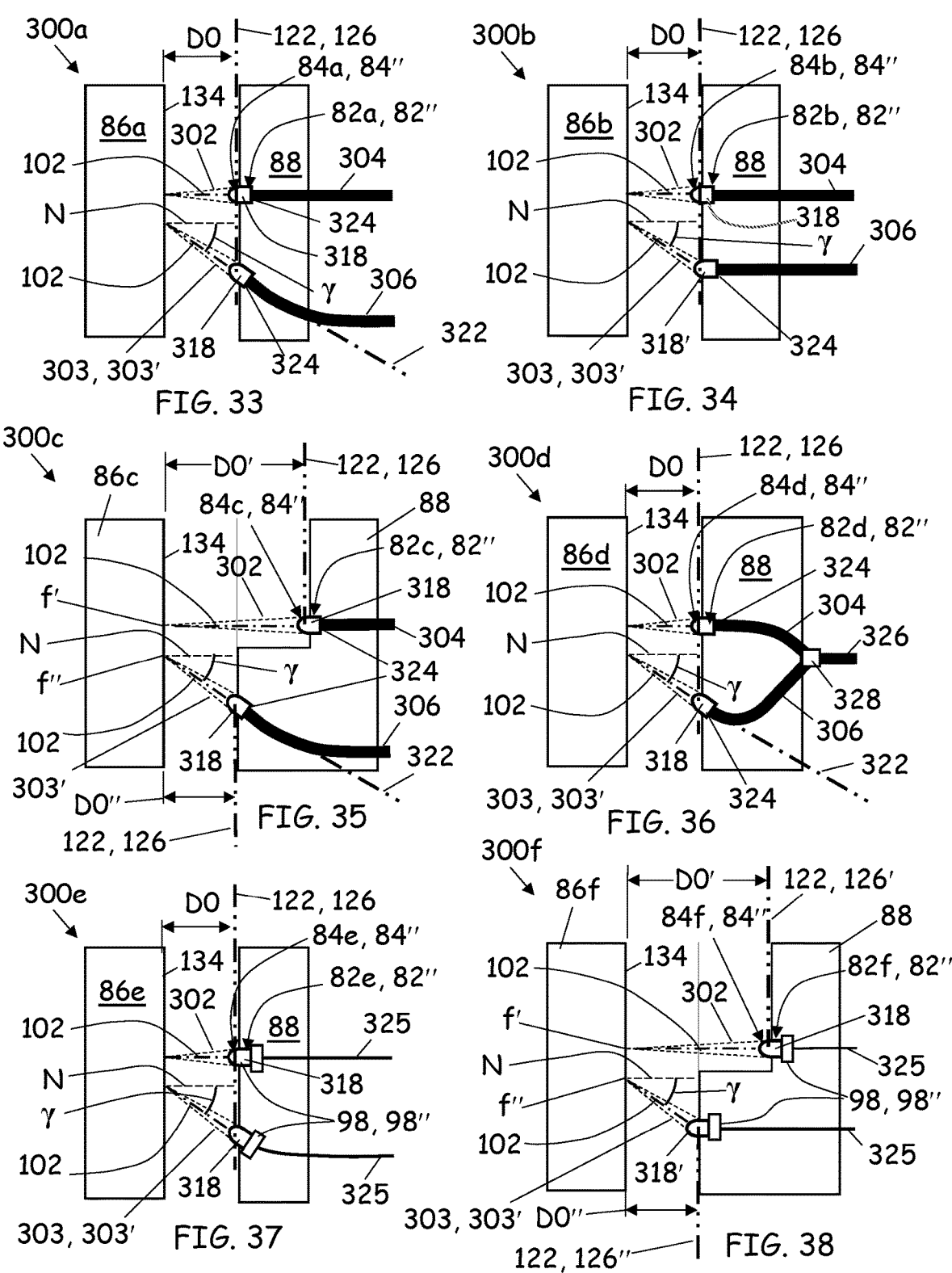
FIG. 33 is a schematic of the dual beam configuration of FIG. 31 according to an embodiment of the disclosure.
FIGS. 34 through 38 are schematics of alternative dual beam configurations for use with the force sensing catheter of FIG. 21 according to embodiments of the disclosure.

Specific dual beam configurations 300a through 300f are schematically depicted at FIGS. 33 through 38, according to embodiments of the disclosure. A dual beam configuration 300a is depicted at FIG. 33, representing the configuration of the layout described attendant to FIG. 34. A characteristic of the dual beam configuration 300a is that, while the optical fiber 304 may extend normal to the designated plane 126, the optical mount 88 is configured to orient the optical fiber 306 so that an optical fiber axis 322 defined at an optical fiber termination 324 of the optical fiber 306 is aligned to with the incidence angle γ defined by optical arrangement 84".

Referring to FIG. 34, a dual beam configuration 300b that includes the optical fibers 304 and 306 in a parallel arrangement approaching the emitter assembly 82b is depicted according to an embodiment of the disclosure. Unlike the dual beam configuration 300a, the optical mount 88 orients both optical fibers 304 and 306 so that the optical fiber axes 322 are normal to the designated plane 126, The optical arrangement component(s) 318' associated with optical fiber 306 is configured to redirect the beam 303 at the incidence angle γ. In some embodiments, the optical arrangement component(s) 318' are integral, having been formed as a lens from the optical fiber 304 itself. The optical arrangement components 318 may include an optical waveguide or a prism to accomplish the redirection, with a lens for shaping and focusing the beam 303. In some embodiments, a single optical arrangement component 318 combines the function of deflection and focusing the beam 303.

Functionally, the optical fibers 304 and 306 can extend into and through the optical mount 88 in parallel fashion for a simpler design that is less prone to manufacturing uncertainties. The parallel optical fibers 304 and 306 also require less cross section at the optical mount 88, providing more cross-section at the distal end portion 44 for other aspects of catheter operation, such as irrigation channel termination and power lead connections for the ablation head 68. The parallel arrangement avoids excessively small bend radii of the optical fibers 304, 306 that would otherwise impact optical fiber performance.

Referring to FIG. 35, a dual beam configuration 300c is depicted according to an embodiment of the disclosure. The optical fiber terminations 324, optical arrangement components 318, and optical fibers 304 and 306 of the dual beam configuration 300c are at different axial locations, thereby effectively defining different designated planes 126' and 126". The different designated planes 126' and 126" result in the definition of different baseline axial separation distances D0' and D0". To accommodate the different axial separation distances D0' and D0", the associated optical arrangement components 318 may define different focal points f' and f".

Functionally, the longer axial separation distance D0' enables the beam 302 to define a narrower profile angle α and a longer focal length, thereby producing a smaller irradiation shape akin to the irradiation spots Cj' of the multiple beam profiles 200c and 200d (FIGS. 17 and 18). Also, the narrower profile angle α enables the irradiation spots Cj to remain smaller over a greater range of dynamic axial separation D. As discussed below attendant to FIGS. 39 through 42, this combination of aspects has utility for the dual beam configurations 300.

Referring to FIG. 30, a dual beam configuration 300d that sources the optical fibers 304 and 306 from a single optical fiber 326 is depicted according to an embodiment of the disclosure. The dual beam configuration 300d includes a splitting component 328 at a junction of the single optical fiber 326 and the optical fibers 304 and 306, the splitting component 328 routing electromagnetic radiation to both. The splitting component 328 may comprise, for example, a beam splitter, a DOE, optical waveguides, or prisms. In some embodiments, more than the two beams 302 and 303 may be implemented, and the splitting component 328 divides the sourced electromagnetic radiation accordingly. In some embodiments (not depicted), the transfer of electromagnetic irradiation to emitter assembly 82d and/or the optical arrangement 84d for dual beam configuration 300d is accomplished without the use of the fiber optics 304 and 306; instead, the electromagnetic radiation may be propagated across a gap.

Functionally, sourcing the emitter assembly 82d from a single optical fiber 326 reduces the cross-section required to deliver the electromagnetic radiation, thereby enabling a reduction in the diameter of the catheter shaft 42 and/or more cross-section for other aspects of the force sensing catheter 40, such as irrigation channels and power leads for the ablation head 68.

Referring to FIGS. 37 and 38, dual beam configurations 300e and 300f utilizing direct or local emitters 98 are depicted according to embodiments of the disclosure. As with the beam configurations 200, the electromagnetic radiation is sourced locally using electrical energy. The dual beam configuration 300e is similar to the dual beam configuration 300a, with distributed emitters 98″ being substituted for the optical fiber terminations 324, and electrical conductors 325 being substituted for the optical fibers 306 and 308. For the dual beam configuration 300e, the optical mount 88 is configured to align one of the emitters 98 at the incidence angle γ. The dual beam configuration 300f combines the different axial separation distances D0′ and D0″ aspect of the dual beam configuration 300c and the redirecting optical arrangement component(s) 318′ of the dual beam configuration 300b to establish the incidence angle γ. It is also contemplated to use optical fiber links (not depicted) between the emitter assemblies 82 and the optical arrangement 84 for the dual beam configurations 300e and 300f, the fiber optic link being sourced by a single local emitter 98.

The substitution of various components, such as described for dual beam configurations 300e and 300f, demonstrates the modularity of the various force sensor assemblies 52 disclosed herein. A skilled artisan, in view of the totality of this disclosure, is able to derive embodiments that are not depicted herein. As such, non-depicted embodiments that implement aspects from the various depicted embodiments are within the scope of this disclosure.

Figures 39, 40, 41, 42, 43, 44:
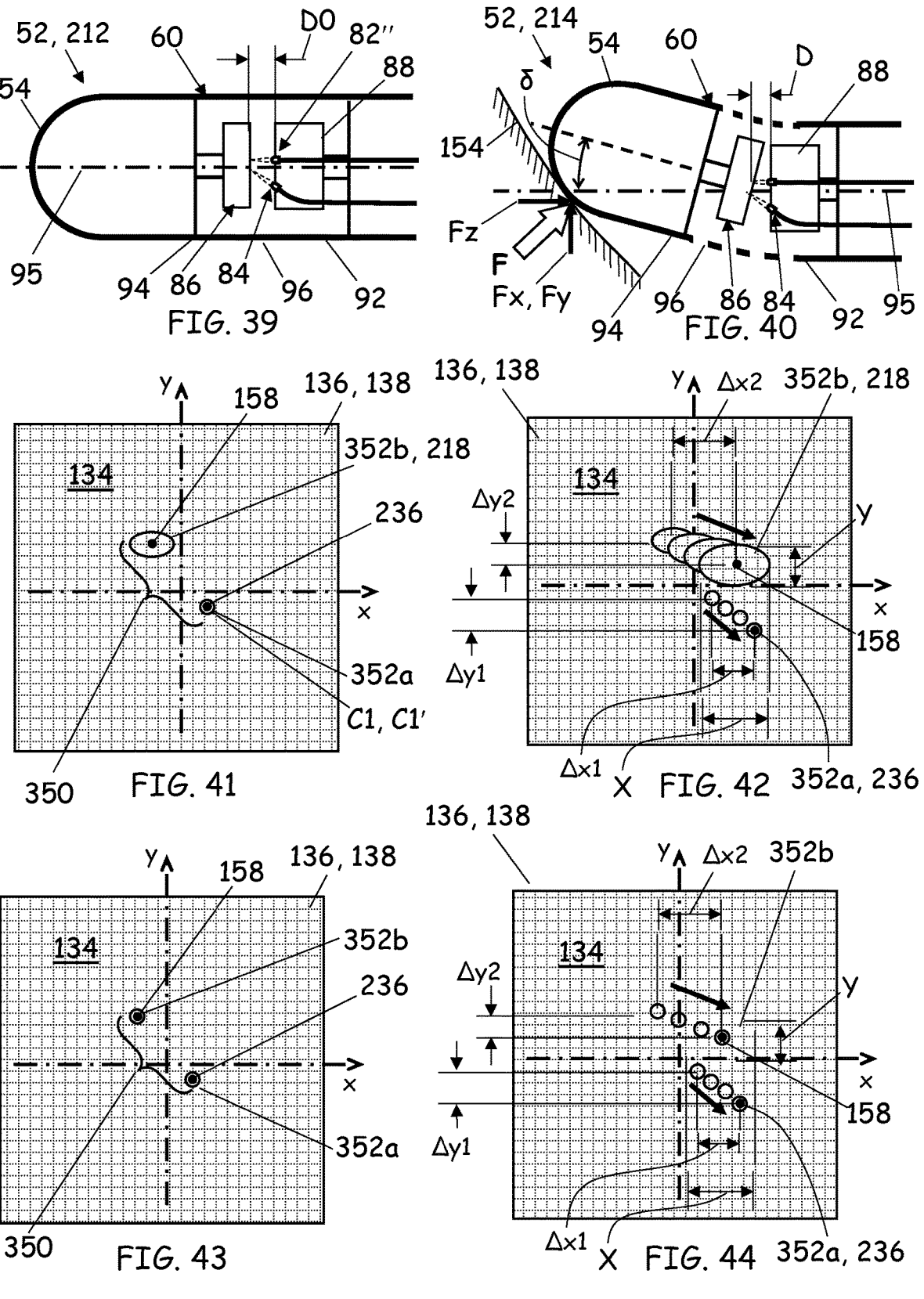
FIG. 39 is a schematic of the force sensor assembly utilizing the dual beam configuration of FIG. 33 in an unloaded state according to an embodiment of the disclosure.
FIG. 40 is a schematic of the force sensor assembly of FIG. 39 in a loaded state according to an embodiment of the disclosure.
FIG. 41 is a plan view of an irradiation pattern incident on the focal plane of the force sensor assembly of FIG. 39 according to an embodiment of the disclosure.
FIG. 42 is a plan view of the irradiation pattern incident on the focal plane of the force sensor assembly of FIG. 40 according to an embodiment of the disclosure.
FIG. 43 is a plan view of an irradiation pattern of irradiation spots incident on the detection plane of the force sensor assembly as depicted in FIG. 39 according to an embodiment of the disclosure.
FIG. 44 is a plan view of the irradiation pattern of irradiation spots incident on the detection plane of the force sensor assembly as depicted in FIG. 40 according to an embodiment of the disclosure.

Referring to FIGS. 39 through 41, principles of operation for the dual beam configurations 300 are depicted according to embodiments of the disclosure. FIGS. 39 and 41 are representative of the force sensor assembly 52 in the unloaded state 212, whereas FIGS. 40 and 42 are representative of the force sensor assembly 52 in the loaded state 214. An irradiation pattern 350 in the unloaded state 212 is depicted at FIG. 41 and in the loaded state 214 at FIG. 42. For the dual beam configurations as depicted, the irradiation pattern 350 is characterized by two distinct irradiation shapes 352a and 352b. In the depicted embodiment, the irradiation shapes 352a and 352b define a circular and an elliptical shape, respectively. This aspect is non-limiting, as both irradiation shapes 352a and 352b may be the same geometry, for example, both circular or both elliptical.

The irradiation shape 352a may be small in size and define a narrow profile angle α, akin to the designated irradiation spot Cj′ of irradiation patterns 150c, 150d. The depicted embodiment of FIGS. 41 and 42 is an example of such a configuration, where the irradiation shape 352 is also identified as irradiation spot C1 and as the designated irradiation spot C1′, with spot centroid 236. Accordingly, the irradiation shape 352a includes some of the aspects of the multiple beam configurations 200c, 200d, including the advantages of utilizing irradiation spot centroids 236 discussed attendant to FIGS. 17 and 18. The irradiation shape 352b may be larger in size and define larger profile angles α than the irradiation shape 352a. As such, the irradiation shape 352b includes some of the aspects of the beam configurations 200a, 200b, such as the dimensions X and Y, the dynamic distances Δx and Δy, the dynamic changes DX and DY, and the pattern centroids 158 discussed attendant to FIGS. 11 and 12.

The irradiation shape 352a, akin to the designated irradiation spot Cj′ of irradiation patterns 200c, 200d, tracks across the detection plane 134 in response to the dynamic deflection angle δ to define the location change (Δxj, Δyj) of the centroid of the designated irradiation spot Cj′. The dynamic deflection angle δ is caused by non-zero lateral force components Fx and Fy of the reaction force vector F. Accordingly, the lateral force components Fx and Fy may be determined primarily based on the location change (Δxj, Δyj) of the irradiation shape 352a. This effect is illustrated FIG. 42 as the positional change (Δx1,Δy1) of the irradiation shape 352a.

The axial force component Fz causes the distal portion 94 of the deformable body 60 to move toward the proximal portion 92, thereby causing the image sensing module 86 and the optical arrangement 84 to move closer together. Movement of the distal portion 94 toward the proximal portion 92 causes the dynamic change DX and/or DY of the dimension(s) X and/or Y, as described attendant to FIGS. 11 and 12. In addition, the incidence angle γ causes the irradiation shape 352b to shift laterally on the detection plane 134, thereby also incurring a positional change (Δx2,Δy2). Accordingly, the axial force component Fz may be determined based on both size change and the positional change of the irradiation pattern centroid 158 of the irradiation shape 352b, as depicted in FIG. 42.

Referring to FIGS. 43 and 44, an implementation of the dual beam configurations 300 using only position (not beam size) tracking is depicted according to an embodiment of the disclosure. The dual beam configurations 300 may be implemented as a version of the multiple beam configuration 200c, 200d, wherein the beams 100c, 100d are configured to deliver irradiation spots Cj. That is, both irradiation shapes 352a and 352b may be configured as irradiation spots Cj, denoted as irradiation spots C1 and C2 in FIGS. 43 and 44, with C1 being the designated irradiation spot C1′. In this embodiment, the dynamic axial separation D, primarily in response to the axial component Fz, causes the canted beam 303′ to track across the detector plane 134, defining the positional change (Δx2,Δy2) of irradiation spot C2 proportional to Fz. The positional change (Δx2,Δy2) may provide the primary indication of the axial component Fz. The four measured parameters Δx1, Δy1, Δx2, Δy2 provide the requisite minimum of three scalars for resolution of the reaction force vector F into the three components Fx, Fy, and Fz.

For the dual beam configuration 300, the scalar array AU for the unloaded (baseline) state 212 may be represented as in Eq. (2). The scalar array AL for the loaded (dynamic) state 214 may be represented as in Eq. (3). The primary scalars Si, in accordance with the operational principles described above, would be the positional changes ($\Delta$x1,$\Delta$y1) and ($\Delta$x2,$\Delta$y2) and the dynamic changes DX and/or DY. The dynamic changes DX and DY are not depicted in FIG. 42, but instead are depicted at FIG. 12.

As noted in relation to Eqs. (2) and (3), the scalar values Si of the scalar arrays A, or functions thereof, can be linked by conventional calibration techniques wherein a relationship between changes in the irradiation pattern 150 (or vector components directly) and a known force vector applied at the distal tip 54. Examples include, calibration matrix inversion, function fitting, and superposition, and other conventional calibration techniques known to the artisan.

It is noted that the effects described above are primary to the operation of the dual beam configurations 300. Secondary effects may be caused by all the orthogonal force components Fx, Fy, and Fz.

Other catheter forms may be implemented in accordance with the embodiments disclosed herein, such as pigtail (spiral/helix) or basket-like catheters. The skilled artisan, in view of the disclosures presented herein, can readily employ such forms for point-by-point (focal) ablation. As such, these alternate catheter forms are also within the scope of the present disclosure.

Each of the additional figures and methods disclosed herein can be used separately, or in conjunction with other features and methods, to provide improved devices and methods for making and using the same. Therefore, combinations of features and methods disclosed herein may not be necessary to practice the disclosure in its broadest sense and are instead disclosed merely to particularly describe representative and preferred embodiments.

Various modifications to the embodiments may be apparent to one of skill in the art upon reading this disclosure. For example, persons of ordinary skill in the relevant arts will recognize that the various features described for the different embodiments can be suitably combined, un-combined, and re-combined with other features, alone, or in different combinations. Likewise, the various features described above should all be regarded as example embodiments, rather than limitations to the scope or spirit of the disclosure.

Persons of ordinary skill in the relevant arts will recognize that various embodiments can comprise fewer features than illustrated in any individual embodiment described above. The embodiments described herein are not meant to be an exhaustive presentation of the ways in which the various features may be combined. Accordingly, the embodiments are not mutually exclusive combinations of features; rather, the claims can comprise a combination of different individual features selected from different individual embodiments, as understood by persons of ordinary skill in the art.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

Unless indicated otherwise, references to "embodiment(s)", "disclosure", "present disclosure", "embodiment(s) of the disclosure", "disclosed embodiment(s)", and the like contained herein refer to the specification (text, including the claims, and figures) of this patent application that are not admitted prior art.

For purposes of interpreting the claims, it is expressly intended that the provisions of 35 U.S.C. 112(f) are not to be invoked unless the specific terms "means for" or "step for" are recited in the respective claim.

What is claimed is:

1. A force sensor assembly for a percutaneous device, comprising:
a deformable body including a proximal portion and a distal portion, said proximal portion defining and being concentric about a central axis;
an image sensing module physically coupled to one of said proximal portion and said distal portion, said image sensing module including a two-dimensional image sensor that defines a detection plane and an array of pixels;
an emitter assembly physically coupled to another of said distal portion and said proximal portion;
an optical arrangement coupled to said emitter assembly and configured to receive electromagnetic radiation from said emitter assembly,
wherein:
said optical arrangement is configured to form said electromagnetic radiation into a plurality of beams that are subtended by said detection plane of said two-dimensional image sensor to define an irradiation pattern on said two-dimensional image sensor, said irradiation pattern defining a plurality of irradiation spots, each irradiation spot defining a respective irradiation spot centroid;
said deformable body is configured for a deformation in response to a force applied to said distal portion, said deformation including translation of said distal portion along said central axis in response to an axial component of said force and a rotational deflection of said distal portion away from said central axis in response to a lateral force; and
said irradiation pattern dynamically changes on said detection plane in response to said deformation, the dynamic change in said irradiation pattern being detected by said two-dimensional image sensor.

2. The force sensor assembly of claim 1, wherein said dynamic change of said irradiation pattern includes a positional displacement of a designated one of said irradiation spot centroids and a difference between positional displacements of at least two of said irradiation spot centroids.

3. The force sensor assembly of claim 2, wherein at least two of said beams define respective propagation axes that define an open angle that faces said detection plane.

4. The force sensor assembly of claim 3, wherein said plurality of beams intersect between said optical arrangement and said two-dimensional sensor.

5. The force sensor assembly of claim 4, wherein said respective propagation axes substantially intersect between said optical arrangement and said two-dimensional image sensor.

6. The force sensor assembly of claim 4, wherein said optical arrangement is a unitary component.

7. The force sensor assembly of claim 3, wherein said positional displacement of said designated one of said irradiation spot is in response to said rotational deflection of said distal portion.

8. The force sensor assembly of claim 3, wherein said difference between positional displacements of said at least two of said irradiation spot centroids is in response to said translation of said distal portion of said deformable body along said central axis.

9. The force sensor assembly of claim 1, comprising an energy source in communication with said emitter assembly.

10. The force sensor assembly of claim 9, wherein said energy source is one of an electrical source and an electromagnetic radiation source.

11. The force sensor assembly of claim 9, wherein at least one of said emitter assembly, said optical arrangement, and said energy source is configured for selective radiative coupling of at least one individual beam of said plurality of beams with said detection plane.

12. A method for resolving a reaction force vector applied on a percutaneous device, comprising:

configuring a signal processing system for:

receiving a first set of signals from a two-dimensional image sensor of a force sensor assembly that corresponds to a first irradiation pattern that includes a plurality of irradiation spots incident on said two-dimensional image sensor;

receiving a second set of signals from said two-dimensional image sensor that corresponds to a second irradiation pattern that includes said plurality of irradiation spots incident on said two-dimensional image sensor;

determining a change in positions of said plurality of irradiation spots of second irradiation pattern relative to said plurality of irradiation spots of said first irradiation pattern; and inferring a force vector applied to said force sensor assembly based on said change in positions.

13. The method of claim 12, comprising configuring at least two of said irradiation spots of said plurality of irradiation spots to deliver respective beams defining respective propagation axes, said respective propagation axes cooperating to define an open angle that faces a detection plane of said two-dimensional image sensor.

14. The method of claim 13, wherein said respective beams intersect between an optical arrangement and said two-dimensional image sensor.

15. The method of claim 12, comprising configuring said signal processing system for resolving a first set of scalar values that characterize said change in positions.

16. The method of claim 15, wherein said first set of scalar values represent said change in positions based on a change of position of a centroid of an irradiation spot of said first and second irradiation patterns.

17. The method of claim 16, wherein said force vector is inferred using one of calibration matrix inversion, function fitting, superposition of said first set of scalar values.

18. The method of claim 15, comprising configuring said signal processing system for resolving a second set of scalar values, said first set of scalar values characterizing said first irradiation pattern, said second set of scalar values characterizing said second irradiation pattern.

19. The method of claim 18, wherein said first set of scalar values are taken with said force sensor assembly in an unloaded state, and said second set of scalar values are taken with said force sensor assembly in a loaded state.

20. The method of claim 18, wherein said second set of scalar values represent said change in positions based on a change of said second set of scalar values relative to said first set of scalar values.

\* \* \* \* \*